US008138361B2

(12) United States Patent
Ballatore et al.

(10) Patent No.: US 8,138,361 B2
(45) Date of Patent: Mar. 20, 2012

(54) C-10 CARBAMATES OF TAXANES

(75) Inventors: Carlo Ballatore, Philadelphia, PA (US); Angelo J Castellino, San Diego, CA (US); Amos B Smith, III, Merion, PA (US); Joel Desharnais, La Mesa, CA (US); Chengzao Sun, San Marcos, CA (US); Simon E Aspland, Baltimore, MD (US)

(73) Assignees: The Trustees Of The University Of Pennsylvania, Philadelphia, PA (US); Acidophil, LLC, Lutherville, MD (US)

( * ) Notice: Subject to any disclaimer, the term of this patent is extended or adjusted under 35 U.S.C. 154(b) by 792 days.

(21) Appl. No.: 12/158,174

(22) PCT Filed: Dec. 27, 2006

(86) PCT No.: PCT/US2006/049557
§ 371 (c)(1),
(2), (4) Date: Nov. 3, 2008

(87) PCT Pub. No.: WO2007/076160
PCT Pub. Date: Jul. 5, 2007

(65) Prior Publication Data
US 2009/0306014 A1 Dec. 10, 2009

Related U.S. Application Data

(60) Provisional application No. 60/754,434, filed on Dec. 28, 2005.

(51) Int. Cl.
C07D 305/14 (2006.01)
A61K 31/35 (2006.01)
(52) U.S. Cl. .................. 549/510; 549/511; 514/449
(58) Field of Classification Search .............. 549/510, 549/511; 514/449
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,710,795 A | 1/1973 | Higuchi et al. |
| 3,773,919 A | 11/1973 | Boswell et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,674,533 A | 10/1997 | Santus et al. |
| 5,709,874 A | 1/1998 | Hanson et al. |
| 5,733,566 A | 3/1998 | Lewis |
| 5,759,542 A | 6/1998 | Gurewich |
| 5,840,674 A | 11/1998 | Yatvin et al. |
| 5,900,252 A | 5/1999 | Calanchi et al. |
| 5,972,366 A | 10/1999 | Haynes et al. |
| 5,985,307 A | 11/1999 | Hanson et al. |
| 6,004,534 A | 12/1999 | Langer et al. |
| 6,039,975 A | 3/2000 | Shah et al. |
| 6,048,736 A | 4/2000 | Kosak |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,253,872 B1 | 7/2001 | Neumann |
| 6,271,359 B1 | 8/2001 | Norris et al. |
| 6,316,652 B1 | 11/2001 | Steliou |

FOREIGN PATENT DOCUMENTS

WO    WO 2005/030258 A    4/2005

OTHER PUBLICATIONS

Ansel, Introduction to Pharmaceutical Dosage Forms, Fourth Edition, 1985, 126.
Ballatore, C. et al., "A facile route to paclitaxel C-10 carbamates," Bioorg. Chem. Letts., May 16, 2005, 15(10), 2477-2480.
Baloglu, E. et al., "The taxane diterpenoids," J. Nat. Prod., 1999, 62, 1448-1472.
Barron et al., "A fluorescence-based high-throughput assay for antimicrotubule drugs," Anal. Biochem., 2003, 315, 49-56.
"IUPAC-IUB [International Union of Pure and Applied Chemistry-International Union of Biochemistry] Commission of Biochemical Nomenclature. Abbreviated nomenclature of synthetic polypeptides (polymerized amino acids). Revised recommendations (1971)," Biochem., 1972, 11, 942-944.
Buchwald et al., "Long-term, continuous intravenous heparin administration by an implantable infusion pump in ambulatory patients with recurrent venous thrombosis," Surgery, 1980, 88, 507-516.
Ge et al., "Synthesis and interactions of 7-deoxy-, 10-deacetoxy, and 10-deacetoxy-7-deoxypaclitaxel with NCI/ADR-RES cancer cells and bovine brain microvessel endothelial cells," Bioorg. Med. Chem Letts., Nov. 3, 2005, 16(2), 433-436.

(Continued)

*Primary Examiner* — Andrew D Kosar
*Assistant Examiner* — Raymond Covington
(74) *Attorney, Agent, or Firm* — Woodcock Washburn, LLP

(57) ABSTRACT

Provided herein are C-10 taxane carbamates and pharmaceutically acceptable derivatives thereof. In certain embodiments, provided herein are compounds, compositions and methods for treating cancer and taupathy.

37 Claims, No Drawings

OTHER PUBLICATIONS

Goodson, Medical Applications of Controlled Release, 1984, vol. 2, pp. 115-138.

Hoaglin et al., "Performance of Some Resistant Rules for Outlier Labeling," J. Amer. Statistical Assoc., 1986, 81, 991-999.

Langer, "New Methods of Drug Delivery," Science, 1990, 249, 1527-1533.

Ojima, I. et al., Synthesis and Structure-activity relationships of the second-generation antitumor taxoids: Exceptional activity against drug-resistant cancer cells, Journal of Medicinal Chemistry, American Chemical Society, Washington, US, 1996, 39(20), 3889-3896.

Rice, A., et al., "Chemical Modification of Paclitaxel (Taxol) Reduces P-Glycoprotein Interactions and Increases Permeation across the Blood-Brain Barrier in Vitro and in Situ," Journal of Medicinal Chemistry, Jan. 2005, 48, 832-838.

Saudek et al., "A preliminary trial of the programmable implantable medication system for insulin delivery," N. Engl. J. Med., 1989, 321, 574-579.

Sefton, CRC Crit. Ref. Biomed. Eng., 1987, 14(3), 201-240.

Sikic, B.I., "Modulation of multidrug resistance: at the threshold," J. Clin. Oncol., 1993, 11, 1629-1635.

Spletstoser et al., "Single-site chemical modification at C10 of the baccatin III core of paclitaxel and Taxol C reduces P-glycoprotien interactions in bovine brain microvesssel endothelial cells," Bioorg. Med. Chem. Letts., Nov. 10, 2005, 16(3), 495-498.

C-10 CARBAMATES OF TAXANES

CROSS-REFERENCE TO RELATED APPLICATIONS

This application is the National Stage of International Application No. PCT/US2006/049557 filed Dec. 27, 2006, which claims the benefit of U.S. Provisional Application No. 60/754,434, filed Dec. 28, 2005, the disclosure of which is incorporated herein by reference in its entirety.

FIELD

Compounds, compositions and methods for treating cancer and taupathies are provided. The compounds provided are C-10 carbamate derivatives of taxanes.

BACKGROUND

The taxane family of terpenes, of which baccatin III and Taxol® are members, has been the subject of considerable interest in both the biological and chemical arts. Paclitaxel (Taxol®), a cytotoxic natural product, and docetaxel (Taxotere®), a semi-synthetic derivative, are widely used in the treatment of cancer, E. Baloglu and D. G. I. Kingston, *J. Nat. Prod.* 62: 1448-1472 (1999). Paclitaxel and docetaxel have the following structures:

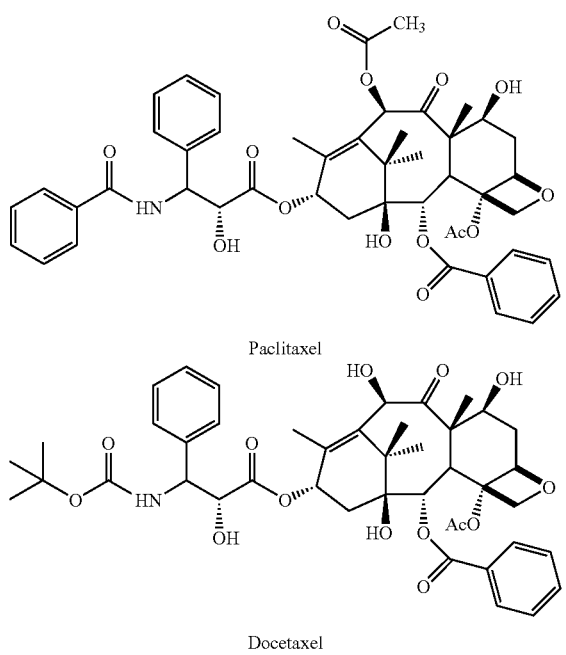

Paclitaxel

Docetaxel

Taxanes are mitotic spindle poisons that inhibit the depolymerization of tubulin, resulting in cell death. While docetaxel and paclitaxel are useful agents in the treatment of cancer, their antitumor activity is limited because of 1) lack of selectivity, 2) poor water solubility, 3) no oral bioavailability, 4) inability to cross the blood-brain-barrier (BBB) and 5) occurrence of drug resistance. Some of these limitations can be at least partially explained with the fact that paclitaxel is a good substrate for P-glycoprotein (Pgp). It has been reported that Pgp is over-expressed (mdr1 gene) in multi-drug resistant (MDR) cancer cells, which binds to cytotoxic (antitumor) agents and pumps them out.

Accordingly, there is a need to develop taxane derivatives that are not substrates for the Pgp expressed in the BBB and have improved efficacy, oral bioavailability and improved drug resistance.

SUMMARY

Provided herein are compounds that are C-10 taxane derivatives, pharmaceutical compositions containing the compounds and methods of use thereof. The compounds are taxanes containing a carbamate moiety at the C-10 position and pharmaceutically acceptable derivatives thereof. The compounds for use in the compositions and methods provided herein have formula 1:

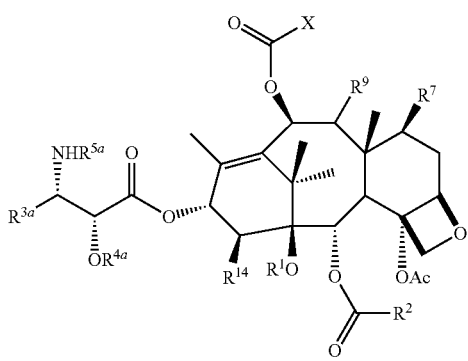

or a pharmaceutically acceptable derivative thereof, wherein $R^1$ is hydrogen, alkyl, alkenyl, alkynyl, cycloalkyl, heterocyclyl, aryl, heteroaryl or acyl;

$R^2$ is alkyl or aryl, wherein the aryl group is optionally substituted with one or more electron withdrawing or electron donating groups;

$R^7$ is H or $OR^{7a}$, where $R^{7a}$, is hydrogen, alkyl, alkenyl, alkynyl, cycloalkyl, heterocyclyl, aryl, heteroaryl, —$COR^{7b}$, —$CONR^{7c}R^{7d}$ or is a hydroxyl protecting group including functional groups which increase the water solubility of the taxoid antitumor agent;

$R^{7b}$ is alkyl, alkenyl, alkynyl, cycloalkyl, heterocyclyl, aryl or heteroaryl, and $R^{7c}$ and $R^{7d}$ are each independently selected as follows:

a) $R^{7c}$ and $R^{7d}$ are each independently hydrogen, alkyl, alkenyl, alkynyl, cycloalkyl, heterocyclyl, aryl or heteroaryl, or b) $R^{7c}$ and $R^{7d}$ together with the nitrogen atom form an optionally substituted 5-7 membered heterocyclic or heteroaryl ring;

$R^9$ is =O or —$OR^{7a}$,

X is $NR^xR^y$, where $R^x$ and $R^y$ are each independently selected as follows:

i) one of $R^x$ or $R^y$ is hydrogen or lower alkyl and the other is selected from carboxyalkyl, carboxyheteroalkyl, carboxyalkenyl, carboxyalkynyl, carboxycycloalkyl, carboxyheterocyclyl, carboxyaryl or carboxyheteroaryl, ii) one of $R^x$ or $R^y$ is hydrogen or lower alkyl and the other is aminoheteroalkyl, wherein the amino group is optionally protected with an amino protecting group, such as a CBZ group;

iii) one of $R^x$ or $R^y$ is hydrogen or lower alkyl and the other is heterocyclyl or alkyl substituted with one or more, in one embodiment one to three, substituents selected from hydroxy, amino, alkylaminocarbonyl, dialkylaminocarbonyl, aralkoxycarbonyl, alkoxycarbonyl, aralkoxycarbonylamino, heterocyclylaminocarbonyl, wherein the heterocyclyl group contains a 5 to 7 membered ring containing one or two heteroatoms selected from N and O and is optionally substituted with 1 to 4 hydroxy or hydroxyalkyl groups, iv) $R^x$ or $R^y$ together with the nitrogen atom from a 5-7 membered heterocyclyl ring containing one or two heteroatoms selected from oxygen and nitrogen;

$R^{14}$ is hydrogen, hydroxyl or alkoxy;

$R^{3a}$ is alkyl, alkenyl, alkynyl, cycloalkyl, heterocyclyl, aryl or heteroaryl;

$R^{4a}$ is hydrogen, alkyl, alkenyl, alkynyl, cycloalkyl, heterocyclyl, aryl, heteroaryl or is a hydroxyl protecting group including functional groups which increase the water solubility of the taxoid antitumor agent; and $R^{5a}$ is $-COR^{7b}$, $-COOR^{7b}$ or $-CONR^{7c}R^{7d}$.

Pharmaceutical compositions containing the compound of formula I and a pharmaceutically acceptable carrier are provided herein.

Also provided are methods for treating cancer by administering compounds and compositions provided herein.

It certain embodiments, provided herein are methods for inhibiting an action of P-glyocoprotein by administering compounds and compositions provided herein.

In other embodiments, provided herein are methods for treatment of taupathies by administering compounds and compositions provided herein. Taupathies include, neurodegenerative diseases such as Alzheimer's disease, tauopathies such as frontotemporoparietal dementia, corticobasal degeneration, Pick's disease and progressive supranuclear palsy.

DETAILED DESCRIPTION OF EMBODIMENTS

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The singular forms "a," "an," and "the" include plural references, unless the context clearly dictates otherwise, Thus, for example, references to a composition for delivering "a drug" include reference to one, two or more drugs.

As used herein "subject" is an animal, typically a mammal, including human, such as a patient.

As used herein "taupathy" (tauopathy) refers to a group of neurodegenerative diseases that have in common increased phoshorylation of tau and accumulation of abnormally phosphorylated tau in the cytoplasm of neurones and glial cells, and in neuronal and glial cell processes. Abnormally hyperphosphorylated tau and neurofilaments accumulate in Alzheimer disease(AD), Pick's disease (PiD), corticobasal degeneration (CBD) and progressive supranuclear palsy (PSP), which are considered the most frequent and representative taupathy. Accumulation of abnormally phosphorylated tau results in characteristic and disease-dependent inclusions in neurones and glial cells, which constitute major structural hallmarks in the pathology of these diseases. In addition, hyperphosphorylated tau isoforms in taupathy produce disease-specific tau bands on Western blots and can be recognised with phosphorylation-specific antibodies.

As used herein, biological activity refers to the in vivo activities of a compound or physiological responses that result upon in vivo administration of a compound, composition or other mixture, Biological activity, thus, encompasses therapeutic effects and pharmacokinetic behaviour of such compounds, compositions and mixtures. Biological activities can be observed in in vitro systems designed to test for such activities.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, cycloalkyl and esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, aralkyl and cycloalkyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl and heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use far treating a cancer.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, $EC_{50}$ refers to a dosage, concentration or amount of a particular test compound that elicits a dose-dependent response at 50% of maximal expression of a particular response that is induced, provoked or potentiated by the particular test compound.

Multi-drug resistance (MDR) is defined as cross-resistance to various structurally different cytotoxic (antitumor) agents, which is caused by increased outward transport of these agents through the plasma membrane by the action of P-glycoprotein as described by Sikic, B. I. in "Modulation of Multidrug Resistance: At the Threshold", *J. Clin. Oncol.*, 11, 1629-1635, 1993. In other words, P-glycoprotein is overexpressed (mdr1 gene) in MDR cancer cells, which binds to cytotoxic (antitumor) agents and pumps them out.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, ethene, propene, butene, pentene, acetylene and hexyne. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "heteroalkyl" refers to a straight, branched or cyclic, in certain embodiments straight or branched, aliphatic hydrocarbon group having, inserted in the hydrocarbon chain one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY', where Y and Y' are each independently hydrogen, alkyl, aryl, heteroaryl, cycloalkyl or heterocyclyl, in one embodiment having from 1 to about 20 atoms, in another embodiment having from 1 to 12 atoms in the chain.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups nay, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, generally selected from $Q^1$.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, generally selected from $Q^1$.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyano, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_2$O—.

As used herein, "carboxy" refers to a divalent radical, —C(O)O—,

As used herein, "aminocarbonyl" refers to —C(O)NH$_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "diarylaminocarbonyl" refers to —C(O)NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl, As used herein, "aryloxyl" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene, There may be optionally inserted along the alkylene group one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY', where Y and Y' are each independently hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, —(CRR)$_n$—S(=O)—(CRR)$_m$—, and —(CRR)$_n$—S(=O)$_2$—(CRR)$_m$—, where n and m are each independently an integer from 0 to 4. In certain embodiments herein, the "R" groups in the definitions of azaalkylene, oxaalkylene and thiaalkylene are each independently selected from hydrogen and Q$^1$, as defined herein, As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, ill another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylenie" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C=C—(CH$_2$)$_n$—C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "substituted alkylene," "substituted alkenylene," "substituted alkynylene," "substituted cycloalkylene," "substituted cycloalkenylene," and "substituted cycloalkynylene" refer to alkylene, alkenylene, alkynylene, cycloalkylene, cycloalkenylene and cycloalkynylene groups, respectively, that are substituted with one or more substituents, in certain embodiments one to three or four substituents, where the substituents are as defined herein, generally selected from Q$^1$.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 5 or 6 carbons.

As used herein, "heteroarylene" refers to a divalent monocyclic or multicyclic aromatic ring system, in one embodiment of about 5 to about 15 members where one or more, in certain embodiments 1 to 3, of the atoms in the ring system is a heteroatom, that is, an element other than carbon, including but not limited to, nitrogen, oxygen or sulfur.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted arylene," "substituted heteroarylene" and "substituted heterocyclylene" refer to arylene, heteroarylene and heterocyclylene groups, respectively, that are substituted with one or more substituents, in certain embodiments one to three of four substituents, where the substituents are as defined herein, generally selected from $Q^1$.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$), As used herein, "arylalkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC(S)NH—. As used herein, aminocarbonyl refers to —NHC(O) group. As used herein, aminocarbonyloxy refers to —NHC(O)O— group.

As used herein, "semicarbazide" refers to —NHC(O)NHNH, "thiosemicarbizide refers to —NHC(S)NHNH. "Carbazate" refers to the divalent group —OC(O)NHNH—. "Issothiocarbazate" refers to the divalent group —SC(O)NHNH—. "Thiocarbazate" refers to the divalent group —OC(S)NHNH—. "Sulfonylhydrazide" refers to the group —SO$_2$NHNH—. "Hydrazide" refers to the divalent group —C(O)NHNH—. "Azo" refers to the divalent group —N═N—. "Hydrazinyl" refers to the divalent group —NH—NH—.

Where the number of any given substituent is not specified (e.g., "haloalkyl"), there may be one or more substituents present. For example, "haloalkyl" may include one or more of the same or different halogens. As another example, "C$_{1-3}$alkoxyphenyl" may include one or more of the same or different alkoxy groups containing one, two or three carbons.

In naming the compounds, the abbreviated name of the taxane, such as PXL for paclitaxel is followed by the point of attachment and functionality linking the taxane various groups, for example, amines, optionally via linking atoms interspaced inbetween. The point of attachment in the compounds provided herein is C10 and the functionality linking the taxane to the other groups is a carbamate moiety. Thus, the designation PXL-10Ca in the nomenclature of the compounds provided herein indicates paclitaxel derivatives with carbamate functionality at the C10 position. The linking group, when present, between the carbamate functionality of the taxane and the attached moiety is indicated as a prefix to the attached moiety as an abbreviation. For example, compound PXL-10Ca-ALK(6)Arm(2)-glucosamine is a paclitaxel glucosamine derivative, wherein the glucosamine at 2 position is linked via an amide bond to paclitaxel C10 carbamate functionality with a C6 alkane unit.

Exemplary linkers and the abbreviations used in the compounds herein are as follows:

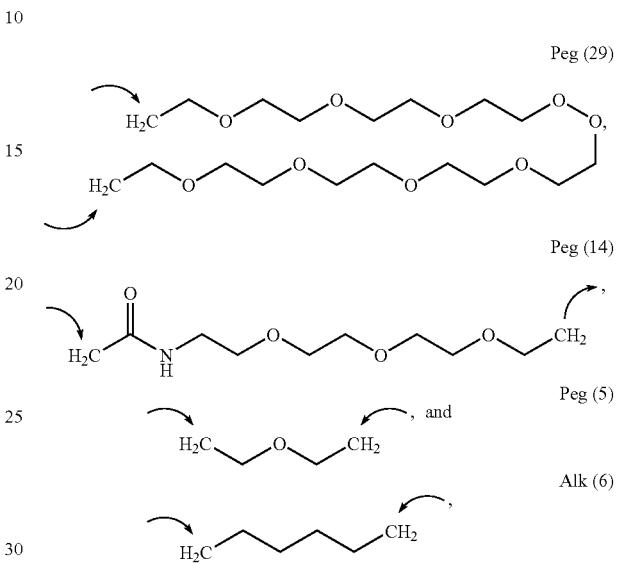

Arrows indicate site of attachment to C10 carbamate of taxane and to the moiety attached thereto.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11; 942-944). For example, the following terms have their accepted meaning in the chemical literature:

| | |
|---|---|
| AcOH | acetic acid |
| CHCl$_3$ | chloroform |
| conc | concentrated |
| DBU | 1,8-diazabicyclo[5.4.0]undec-7-ene |
| DIEA | N-ethyl-N,N-di-isopropylamine |
| DCM | dichloromethane |
| DME | 1,2-dimethoxyethane |
| DMF | N,N-dimethylformamide |
| DMSO | dimethylsulfoxide |
| EtOAc | ethyl acetate |
| EtOH | ethanol (100%) |
| Et$_2$O | diethyl ether |
| Hex | hexanes |
| H$_2$SO$_4$ | sulfuric acid |
| MeCN | acetonitrile |
| MeOH | methanol |
| Pd/C | palladium on activated carbon |
| TEA | tiriethylamine |
| THF | tetrahydrofuran |
| TFA | trifluoroacetic acid |
| Cbz | benzyloxycarbonyl |
| CDI | 1,1'-carbonyldiimidazole |
| DCM | dichloromethane |
| DIEA | N,N-diisopropylethylamine |
| DMAP | 4-(dimethylamino)pyridine |
| DMF | N,N-dimethylformamide |
| IPA | isopropyl alcohol |
| MeOH | methanol |
| MS | mass spectroscopy |

-continued

| | |
|---|---|
| RP-HPLC | reversed phase high performance liquid chromatography |
| RT | room temperature |
| TEA | triethylamine |
| TFA | trifluoroacetic acid and |
| Ts | Tosyl. |

B. Compounds

In certain embodiments, the compounds provided have formula I, wherein
$R^1$ is hydrogen or alkyl;
$R^2$ is alkyl or aryl group, wherein the aryl group is optionally substituted with one or more electron withdrawing group, such as F, $NO_2$, CN, Cl, $CHF_2$, and $CF_3$, or electron donating groups, such as $OCH_3$, $OCH_2CH_3$, $NR^eR^f$ and $OR^g$;
$R^{7e}$ and $R^{7f}$ are each independently alkyl, cycloalkyl or aryl;
$R^{7g}$ is alkyl or cycloalkyl;
$R^7$ is H or $OR^{7a}$, where $R^{7a}$ is hydrogen, hydroxyl protecting group, alkyl, cycloalkyl, heterocyclyl, aryl, heteroaryl, alkylcarbonyl or —$CONR^{7c}R^{7d}$;
$R^{7b}$ is alkyl, alkenyl, alkynyl, cycloalkyl, heterocyclyl, aryl or heteroaryl;
$R^{7c}$ and $R^{7d}$ are each independently selected as follows:
  a) $R^{7c}$ and $R^{7d}$ are each independently hydrogen, alkyl, alkenyl, alkynyl, cycloalkyl, heterocyclyl, aryl or heteroaryl; or
  b) $R^{7c}$ and $R^{7d}$ together with the nitrogen atom form an optionally substituted 5-7 membered heterocyclic or heteroaryl ring;
$R^9$ is =O, OH or alkoxy;
X is $NR^xR^y$, where $R^x$ and $R^y$ are each independently selected from
  i) one of $R^x$ or $R^y$ is hydrogen and the other is selected from carboxyalkyl, carboxyheteroalkyl, carboxyalkenyl, carboxyalkynyl, carboxycycloalkyl, carboxyheterocyclyl, carboxyaryl and carboxyheteroaryl,
  ii) aminoheteroalkyl, wherein the amino group is optionally protected with an amino protecting group, such as a CBZ group;
  iii) one of $R^x$ or $R^y$ is hydrogen and the other is heterocyclyl or alkyl substituted with one or more, in one embodiment one to three substituents selected from hydroxy, amino, alkylaminocarbonyl, dialkylaminocarbonyl, aralkoxycarbonyl, alkoxycarbonyl, aralkoxycarbonylamino, and heterocyclylaminocarbonyl, wherein the heterocyclyl group contains a 5 to 7 membered ring containing one or two heteroatoms selected from N and O and is optionally substituted with 1 to 4 hydroxy or hydroxyalkyl groups,
$R^{14}$ is hydrogen;
$R^{3a}$ is alkyl, alkenyl or aryl;
$R^{4a}$ is hydrogen;
$R^{5a}$ is alkloxycarbonyl or arylcarbonyl.
In certain embodiments, $R^1$, $R^2$, $R^{3a}$, $R^{4a}$, $R^{5a}$, $R^{7a}$, $R^{7b}$, $R^{7c}$, $R^{7d}$, $R^x$, $R^y$, $R^{14}$, and R are unsubstituted or substituted with 1-4 substituents, each independently selected from $Q^1$, wherein
$Q^1$ is halo, pseudohalo, hydroxy, oxo, thia, nitrile, nitro, formyl, mercapto, hydroxycarbonyl, hydroxycarbonalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonlylalkyl, arylcarbonylalkyl, aminocarbonyl, alkylaminocarbonyl, dialkylaminocarbonyl, arylaminocarbonyl, arylaminocarbonyl, diary aminocarbonyl, arylalkylaminiocarbonyl, alkoxy, aryloxy, heteroaryloxy, heteroaralkoxy, heterocyclyloxy, cycloalkoxy, perfluoroalkoxy, alkenyl oxy, alkynyloxy, aralkoxy, alkylcarbonyloxy, arylcarbonyloxy, aralkylcarbonyloxy, alkoxylcarbonyloxy, aryloxycarbonyloxy, aralkoxycarbonyl oxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylurcido, N',N'-diarylureido, N'-arylureido, N,N'-dialkylureido, N-alkyl-N'-aryl ureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkyl aminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkyl carbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonyl amino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyl oxy, dialkylaminosulfonyl oxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alklarylaminosulfonyl; or two $Q^1$ groups, which substitute atoms in a 1, 2 or 1,3 arrangement, together form alkylenedioxy (i.e., —O—$(CH_2)_y$—O—), thioalkylethoxy (i.e., —S—$(CH_2)_y$O—) or alkylenedithioxy (i.e., —S—$(CH_2)_y$—S—) where y is 1 or 2; or two $Q^1$ groups, which substitute the same atom, together form alkylene; and
each $Q^1$ is independently unsubstituted or substituted with one, two or three substituents, each independently selected from $Q^2$;
each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkyl carbonyloxy, arylcarbonyloxy, aralkylcarbonyloxy, alkoxycarbonyloxy, aryloxycarbonyloxy, aralkoxycarbonyloxy, aminocarbonyloxy, alkyl amoinocarbonyloxy, dialkylaminocarbonyloxy, alkylarylaminocarbonyloxy, diary)aminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkyl ureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonyl amino, alkoxycarbonylamino, aralkoxycarbonylamino, arylcarbonylamino, arylcarbonylaminoalkyl, aryloxycarbonylaminoalkyl, aryl oxyarylcarbonylamino, aryloxycarbonylamino, alkylsulfonylamino, aryl sulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfonyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two Q$^2$ groups, which substitute atoms in a 1, 2 or 1,3 arrangement, together form alkylenedioxy (i.e., —O—(CH$_2$)$_y$—O—), thioalkylenoxy (i.e., —S—(CH$_2$)Y—O—) or alkylenedithioxy (i.e., —S—(CH$_2$)$_y$—S—) where y is 1 or 2; or two Q$^2$ groups, which substitute the same atom, together form alkylene.

R$^{50}$ is hydroxy, alkoxy, aralkoxy, alkyl, heteroaryl, heterocyclyl, aryl or —NR$^{70}$R$^{71}$, where R$^{70}$ and R$^{71}$ are each independently hydrogen, alkyl, aralkyl, aryl, heteroaryl, heteroaralkyl or heterocyclyl, or R$^{70}$ and R$^{71}$ together form alkylene, azaalkylene, oxaalkylene or thiaalkylene;

R$^{51}$, R$^{52}$ and R$^{53}$ are each independently hydrogen, alkyl, aryl, aralkyl, heteroaryl, heteroaralkyl, heterocyclyl or heterocyclylalkyl;

R$^{60}$ is hydrogen, alkyl, aryl, aralkyl, heteroaryl, heteroaralkyl, heterocyclyl or heterocyclylalkyl; and R$^{63}$ is alkoxy, aralkoxy, alkyl, heteroaryl, heterocyclyl, aryl or —NR$^{70}$R$^{71}$.

In certain embodiments, Q$^1$ is halo, pseudohalo, hydroxy, oxo, thia, nitrile, amino, nitro, formyl, mercapto, hydroxycarbonyl, hydroxycarbonylalkyl, alkyl, haloalkyl, aminoalkyl, diaminoalkyl, cycloalkyl, cycloalkylalkyl, heterocyclyl, heterocyclylalkyl, aryl, heteroaryl, aralkyl, heteroarylalkyl, alkylcarbonyl, aryl carbonyl, heteroarylcarbonyl, alkoxycarbonyl, aralkyloxycarbonyl, ralkoxycarbonylanimo, aminocarbonyl, alkoxy, aryloxy, heteroaryloxy, heteroaralkoxy, heterocyclyloxy, cycloalkoxy, aralkoxy, alkylamino, dialkylamino, haloalkylamino, arylamino, diarylamino or alkylarylamino.

The hydroxyl protecting group for use herein are known in the art and include, but are not limited to methoxylmethyl (MOM), methoxyethyl (MEM), 1-ethoxyethyl (EE), benzyloxymethyl, (β-trimethylsilylethoxyl)-methyl, tetrahydropyranyl, 2,2,2-trichloroethoxylcarbonyl (Troc), benzyloxycarbonyl (CBZ), tert-butoxycarbonyl (t-BOC), 9-fluorenylmethoxycarbonyl (Fmoc), 2,2,2-trichloroethoxymethyl trimethylsilyl, triethylsilyl, tripropylsilyl, dimethylethylsilyl, dimethyl(t-butyl)silyl, diethylmethylsilyl, dimethylphenylsilyl, diphenylmethylsilyl, acetyl, chloroacetyl, dichloroacetyl, trichoroacetyl and trifluoroacetyl.

In certain embodiments, the compounds provided have formula I, wherein

R$^1$ is hydrogen;

R$^2$ is alkyl or aryl group, optionally substituted with one, two or three substituents selected from F, NO$_2$, CN, Cl, CHF$_2$, CF$_3$, OCH$_3$, OCH$_2$C$_3$, NR$^e$R$^f$ and OR$^g$;

R$^7$ is H, alkoxy, acyl, aryloxy, alkylaminocarbonyl, dialkylaminocarbonyl or carboxyalkylcarbonyl;

R$^9$ is =O,

X is NR$^x$R$^y$, where R$^x$ and R$^y$ are each independently selected from i) one of R$^x$ or R$^y$ is hydrogen and the other is selected from carboxyalkyl, carboxyheteroalkyl, carboxyalkenyl, carboxyalkynyl, carboxycycloalkyl, carboxyheterocyclyl, carboxyaryl and carboxyheteroaryl;

ii) aminoheteroalkyl, wherein the amino group is optionally protected with an amino protecting group, such as a CBZ group;

iii) one of R$^x$ or R$^y$ is hydrogen and the other is heterocyclyl or alkyl substituted with one or more, in one embodiment one to three substituents selected from hydroxyl, amino, alkylaminocarbonyl, dialkylaminocarbonyl, aralkoxycarbonyl, alkoxycarbonyl, aralkoxycarbonylamino, and heterocyclylaminocarbonyl, wherein the heterocyclyl group contains a 5 to 7 membered ring containing one or two heteroatoms selected from N and O and is optionally substituted with 1 to 4 hydroxy or hydroxyalkyl groups;

R$^{14}$ is hydrogen;

R$^{4a}$ is hydrogen;

R$^{3a}$ is alkyl, alkenyl or aryl; and

R$^{5a}$ is alkoxycarbonyl or arylcarbonyl.

In one embodiment, R$^1$ is hydrogen or alkyl. In another embodiment, R$^1$ is hydrogen.

In certain embodiments, R$^2$ is lower alkyl or aryl. In certain embodiments, the aryl group of R$^2$ is substituted with one, two, three or four electron withdrawing or electron donating groups. Such groups are known in the art and include, but are not limited to, electron withdrawing groups: F, NO$_2$, CN, Cl, CHF$_2$, and CF$_3$ and electron donating group: —OCH$_3$, —OCH$_2$CH$_3$, alkylamino, dialkylamino, arylamino, diarylamino and alkoxy. In certain embodiments, R$^2$ is optionally substituted phenyl, where the substituents are selected from one to three electron withdrawing or electron donating groups. In one embodiment, R$^2$ is phenyl.

In certain embodiments, R$^7$ is hydrogen, hydroxyl or carbamate. In one embodiment, R$^7$ is hydroxyl.

In one embodiment, R$^9$ is =O. In one embodiment, R$^{14}$ is hydrogen.

In one embodiment, Z$^{3a}$ is aryl, alkyl, haloalkyl, alkenyl or haloalkenyl. In one embodiment, R$^{3a}$ is aryl. In one embodiment, R$^{3a}$ is phenyl.

In one embodiment, R$^{5a}$ is alkoxycarbonyl or arylcarbonyl. In one embodiment, R$^{5a}$ is tert-butyloxycarbonyl or phenylcarbonyl.

In certain embodiments, X is NR$^x$R$^y$, where one of R$^x$ or R$^y$ is hydrogen and the other is carboxyalkyl or dicarboxyalkyl, optionally substituted with one or more groups selected from amino, aryloxyamidoalkyl, aminoalkyl and cycloalkyl. In certain embodiments, R$^x$ is hydrogen and R$^y$ is carboxyalkyl or dicarboxyalkyl, optionally substituted with one or more groups selected from amino, aryloxyamido-alkyl, aminoalkyl and cycloalkyl.

In certain embodiments, X is:
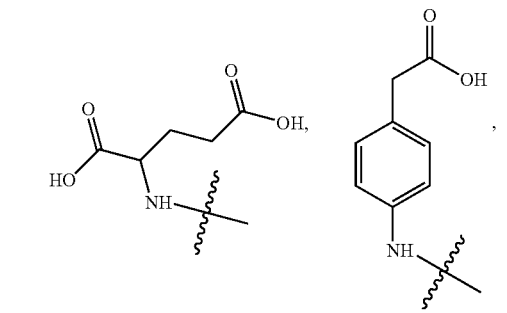
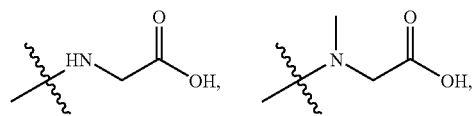
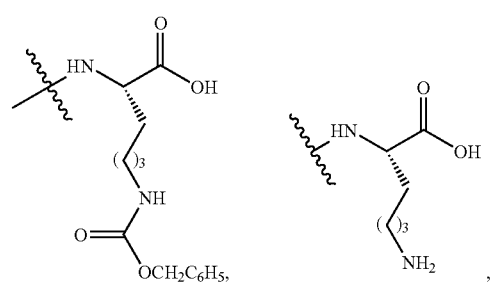
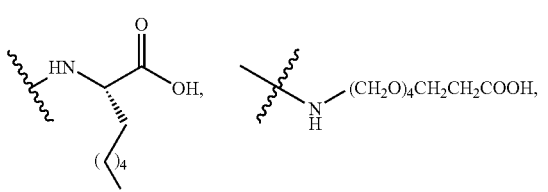
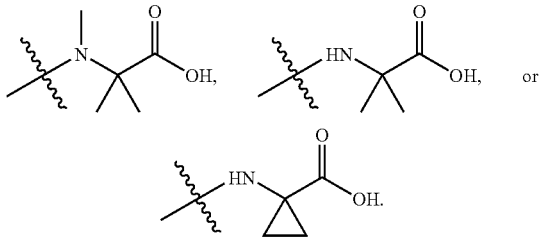
In certain embodiments, X is:
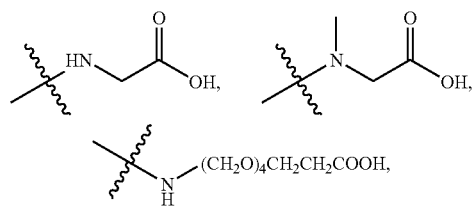
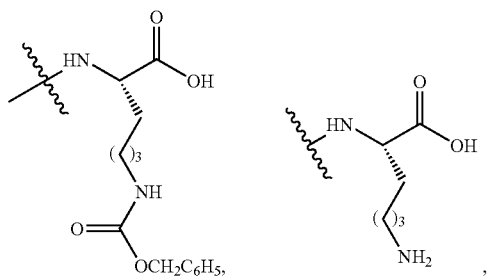
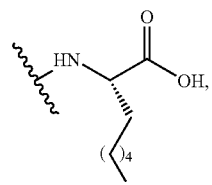
In certain embodiments, X is:
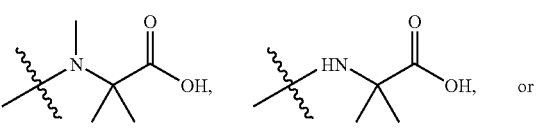
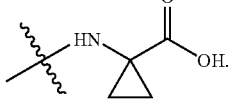
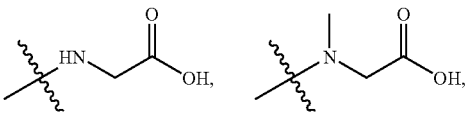
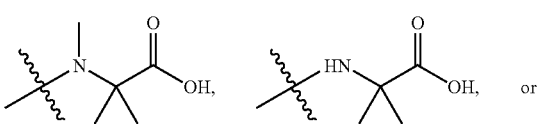
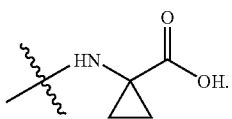
In certain embodiments, X is:
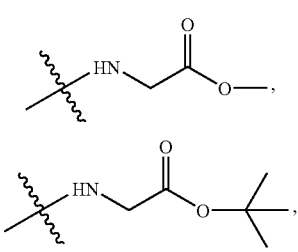

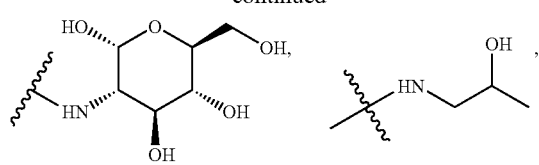

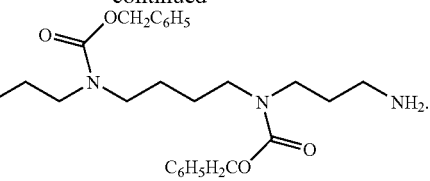

In certain embodiments, X is:

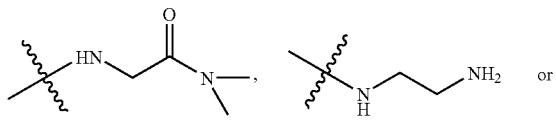

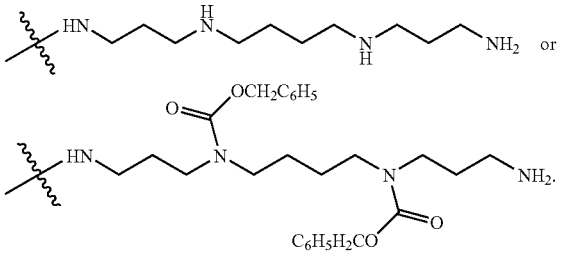

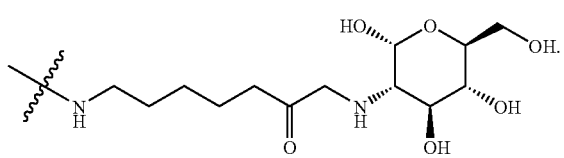

In certain embodiments, the compounds provided herein have formula 1a:

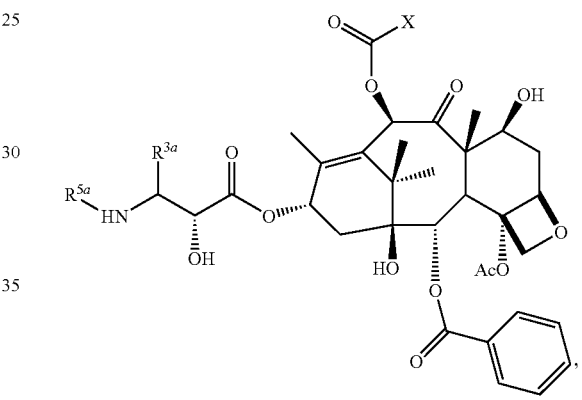

wherein X is $NR^xR^y$, wherein one of $R^x$ or $R^y$ is hydrogen and the other is heterocyclyl or alkyl substituted with one or more, in one embodiment one to three substituents selected from hydroxy, amino, alkylaminocarbonyl, dialkylaminocarbonyl, alkoxycarbonyl and heterocyclylaminocarbonyl, wherein the heterocyclyl group contains a 5 to 7 membered ring containing one or two heteroatoms selected from N and O and is optionally substituted with 1 to 4 hydroxy or hydroxyalkyl groups.

In certain embodiments, the compounds provided herein have formula 1a, wherein X is:

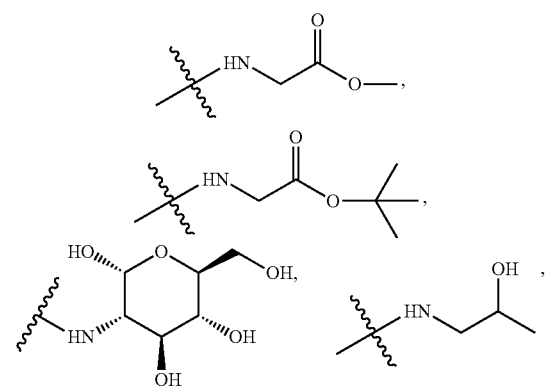

In certain embodiments, X is:

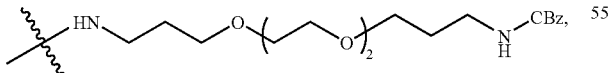

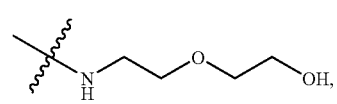

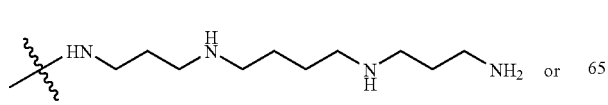

-continued

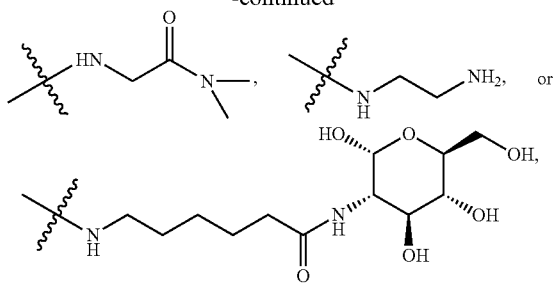

and the variables are as described elsewhere herein.

In certain embodiments, the compounds provided herein have formula 1b:

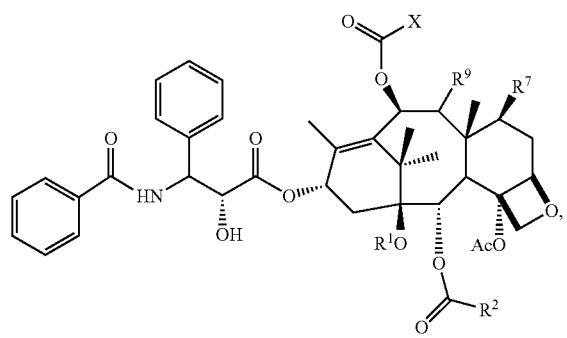

wherein the variables are as described elsewhere herein.

In certain embodiments, the compounds provided herein have formula 1c:

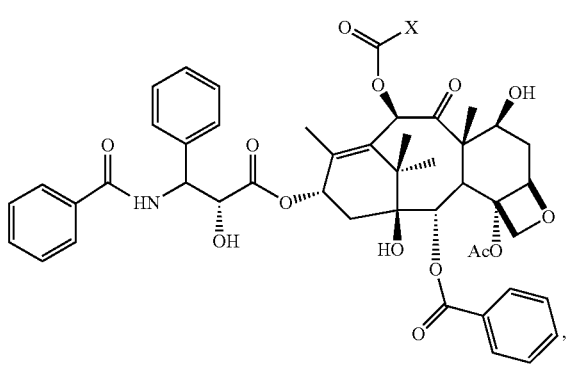

wherein the variables are as described elsewhere herein.

In certain embodiments, the compounds provided herein have formula 1d:

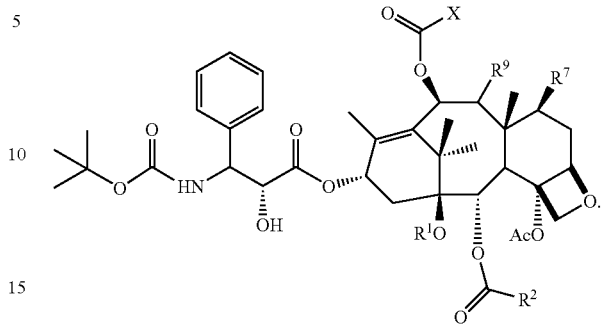

wherein the variables are as described elsewhere herein.

In certain embodiments, the compounds provided herein have formula 1f:

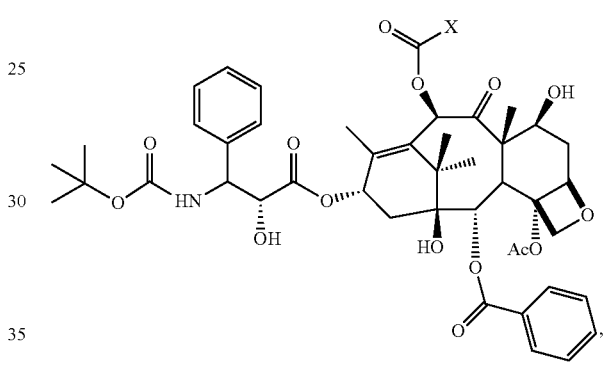

wherein the variables are as described elsewhere herein.

C. Preparation of the C10 Carbamates

A general procedure for preparation of Paclitaxel C10 carbamates as provided herein is illustrated below.

Paclitaxel is protected with TBS-Cl and TES-Cl as illustrated in scheme 1:

Scheme 1

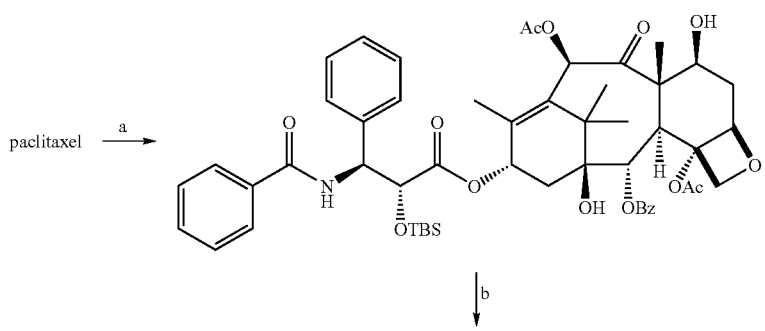

-continued

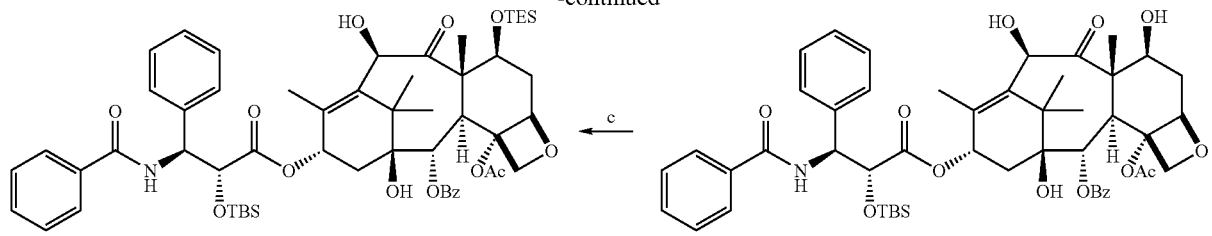

(a) TBS-Cl, dimethylformamide, imidazole, 60° C., 1.5 h; (b) Hydrazine, ethanol, rt, 1.5 h; (c) TES-Cl, DMAP, dichloromethane, rt, 1 h.

As illustrated in Scheme 2, method A, compound 1. can be converted in nearly quantitative yield into its C10 carbonylimidazole 2 by reaction with carbonyl-diimidazole (CDI) in dichloromethane at room temperature. Compound 2 can be reacted with amine Xa in suitable solvents, such as tert-butanol, to yield the corresponding carbamate 3, which can be deprotected to give compound A. Typically, for primary and secondary amines, the reaction can be carried out in non-polar solvents, such as dichloromethane or in protic solvents such as isopropyl alcohol or t-BuOH at elevated temperatures.

In certain embodiments, the C10-carbonylimidazole 2 can be activated with an alkylating agent such as an alkyl halide, alkyl sulfonate or di-alkyl-sulfate to give a $N^1$-alkyl-$N^3$-acyl imidazolium species represented by compound 4 in Method B. In certain embodiments the alkylating agent is selected from dimethylsulfate and methyl iodide. The imidazolium species can then be reacted with various amines either in free or salt forms in protic solvents or aprotic solvents such as DMF, DMSO or dioxane. For amine salts condensation with 4 is conducted in the presence of a hindered base such as DIEA. In certain embodiments, less reactive amines, such as arylamines or heteroarylamines may be condensed with 4 to obtain paclitaxel C10 carbamates with N-aryl or N-heteroaryl linker attachment.

Scheme 2

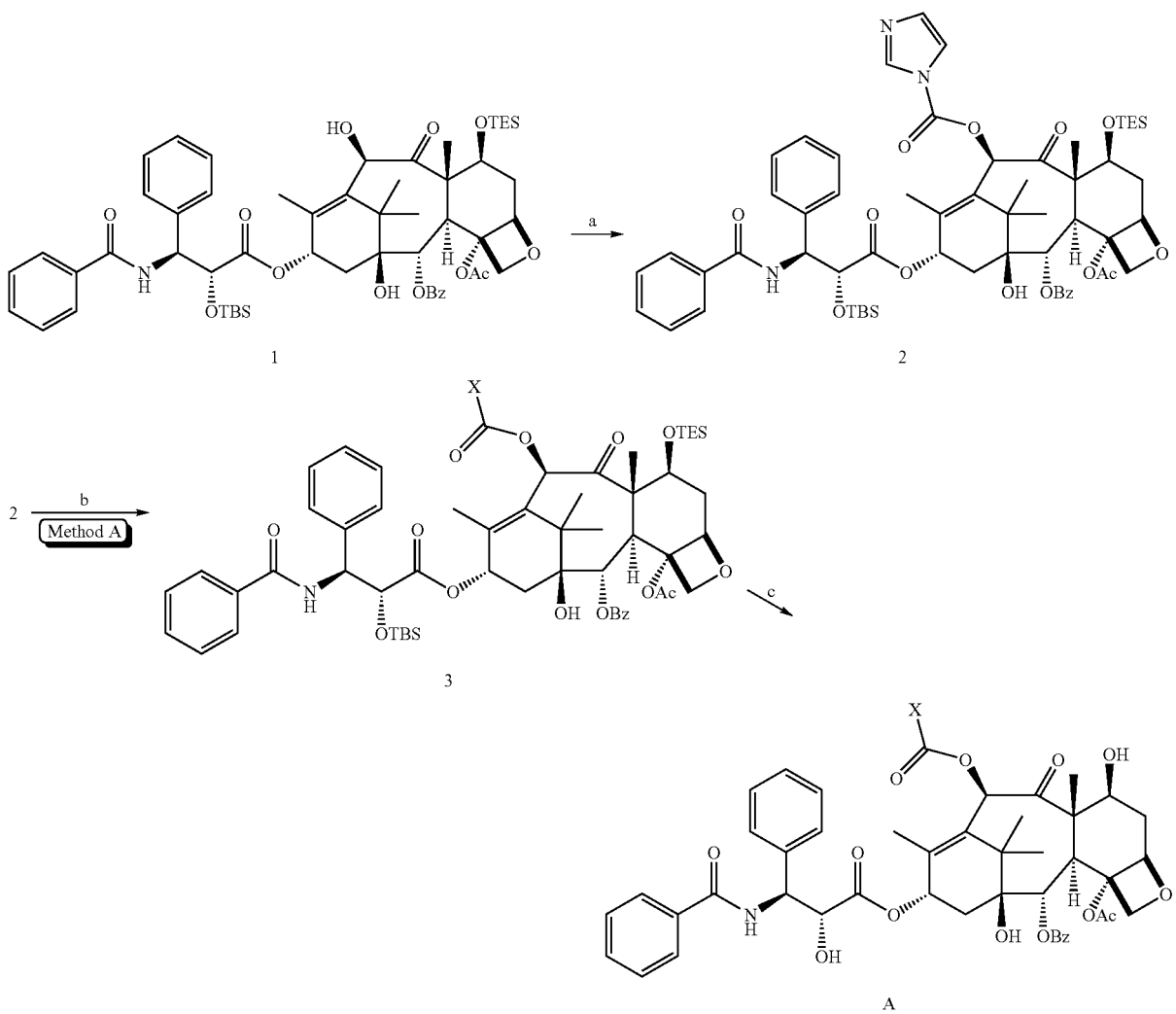

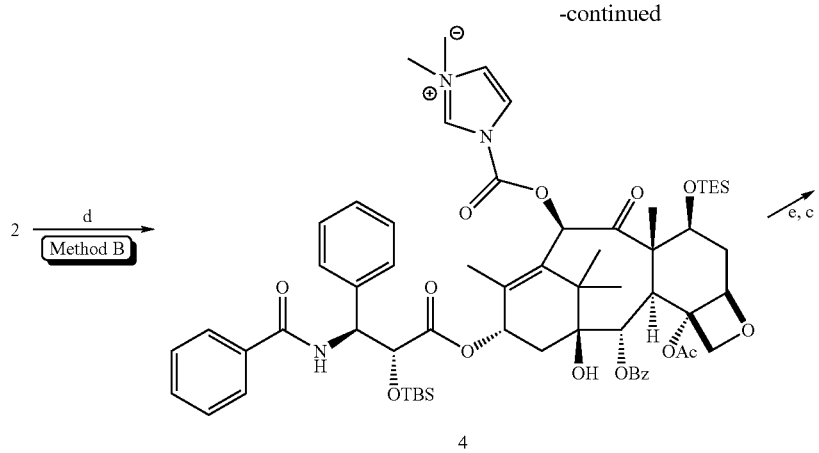

(a) Dichloromethane/carbonyl-diimidazole, rt, 16 h; (b) 5-7 eq. of amine Xa in tert-butanol, 82° C., 16 h; (c) Acetonitrile/pyridine (1:1), HF/Py, 0° C. to rt, 4 h; (d) Methyl iodide/acetonitrile, 55° C., 3 h, (e) 2-3 eq. amine, room temperature.

C-10 carbamate derivatives of other taxanes can be similarly prepared.

D. Formulation of Pharmaceutical Compositions

The pharmaceutical compositions provided herein contain therapeutically effective amounts of one or more of compounds provided herein that are useful in the prevention, treatment, or amelioration of one or more of the symptoms of cancer or taupathies.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to Formulation, as described above. The concentrations of the compounds in the compositions are effective for delivery of an amount, upon administration, that treats, prevents, or ameliorates one or more of the symptoms of conditions associated with cancer or taupathies.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer or taupathies.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in video or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing cancer or taupathies. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically Formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules, Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with cancer or taupathies. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, Such as antacids, H2 blockers, and diuretics. The active ingredient is a compound or pharmaceutically acceptable derivative thereof as described herein. Higher concentrations, up to about 98% by weight of the active ingredient may be included.

Pharmaceutically, acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and poly-vinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/v of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined, 3. Lyophilized Powders Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration, The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123, and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14.201 (1987); Buchwald et al., *Surgery* 88.507 (1980); Saudek et al., *N. Engl. J. Med.* 321: 574 (1989). In another embodiment, polymeric materials can be used. In yet another embodiment, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984). Preferably, a controlled release device is introduced into a subject in proximity of the site of inappropriate immune activation or a tumor. Other controlled release systems are discussed in the review by Langer (*Science* 249:1527-15333 (1990). The active ingredient can be dispersed in a solid inner matrix, e.g., polymethylmethacrylate, polybutylmethacrylate, plasticized or unplasticized polyvinylcchloride, plasticized nylon, plasticized polyethylencterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinyl chloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g. U.S. Pat. Nos. 6,316,652, 6,274,552, 6,271.359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

8. Articles of Manufacture

The compounds or pharmaceutically acceptable derivatives can be packaged as articles of manufacture containing packaging material, a compound or pharmaceutically acceptable derivative thereof provided herein, which is used for treatment, prevention or amelioration of one or more symptoms associated with cancer or taupathies, and a label that indicates that the compound or pharmaceutically acceptable derivative thereof is used for treatment, prevention or amelioration of one or more symptoms of cancer or taupathies.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

E. Evaluation of the Activity of the Compounds

Standard physiological, pharmacological and biochemical procedures are available for testing the compounds to identify those that possess a desired biological activity. In vitro and in vivo assays can be used to evaluate biological activity, such as cytotoxicity and ability to affect rhodamine 123 uptake. Exemplary assays are discussed briefly below.

1. Tubulin Polymerization Assay

The compounds provided herein can be tested in microtubule stabilization assay (Barron, el cal., *Anal. Biochem.* (2003) 315:49-56). Tubulin assembly or inhibition thereof may be monitored by fluorescence using the CytoDYNAMIX Screen™ 10 kit available from Cytoskeleton (1830 S. Acoma St., Denver, Colo.). The kit is based upon an increase in quantum yield of florescence upon binding of a fluorophore to microtubules. Emission is monitored at 405 nm with excitation at 360 nm. The compounds which enhance tubulin assembly will therefore give an increase in emission. Tubulin assembly may also be monitored by light scattering which is approximated by the apparent absorption at 350 nm. In the assay, BSA is employed to prevent aggregation and glycerol, which is a tubulin polymerization enhancer, is omitted from the kit to increase the signal to noise ratio.

2. Rhodamine 123 Uptake Assay

Bovine Brain Endothelial Cells (BBEC) express Pgp and are commonly used as model for Blood Brain Barrier (BBB). Rhodamine 123 is a fluorescent dye which is a good substrate for Pgp. The assay will determine the effect that a given compound has on the rhodamine 123 uptake into BBEC. Any compound interacting with Pgp (either substrate or inhibitor) will cause an increase rhodamine 123 content into the cells. On the other hand if the test compound does not interact with Pgp, then the rhodamine 123 content will remain the same as in the control. It has to be noted that the assay may give false negatives because it cannot distinguish between compounds that are unable to penetrate the cell-membrane from compounds that are able to enter the cells but are not substrate for Pgp.

F. Methods of use of the Compounds and Compositions

Methods of use of the compounds and compositions are also provided. The methods involve both in vitro and in vivo uses of the compounds and compositions.

In certain embodiments, provided herein are methods for inhibiting an action of P-glyocoprotein by administering a compound provided herein or a pharmaceutically acceptable derivative thereof.

In other embodiments, provided are methods for treatment of taupathies, including, but not limited to Alzheimer disease, (AD), Pick's disease (PiD), corticobasal degeneration (CBD), progressive supranuclear palsy (PSP) and frontotemporoparietal dementia.

In certain embodiments, provided are methods for treatment of cancers by administering a compound provided herein or a pharmaceutically acceptable derivative thereof. Examples of cancers include, but are not limited to, non-small cell lung cancer, small cell lung cancer, head and neck squamous cancers, colorectal cancer, prostate cancer, and breast cancer, acute lymphocytic leukemia, adult acute myeloid leukemia, adult non-Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, skin cancer, and small-cell lung cancer. Childhood cancers amenable to treatment by the methods and with the compositions provided herein include, but are not limited to, brain stem glioma, cerebellar astrocytoma, cerebral astrocytoma, ependymoma, Ewing's sarcoma and family of tumors, germ cell tumor, Hodgkin's disease, ALL, AML, liver cancer, medulloblastoma, neuroblastoma, non-Hodgkin's lymphoma, osteosarcoma, malignant fibrous histiocytoma of bone, retinoblastoma, rhabdomyosarcoma, soft tissue sarcoma, supratentorial primitive neuroectodermal and pineal tumors, unusual childhood cancers, visual pathway and hypothalamic glioma, Wilms' tumor, and other childhood kidney tumors.

G. Combination Therapy

The compounds provided herein may be administered as the sole active ingredient or in combination with other active ingredients. Other active ingredients that may be used in combination with the compounds provided herein include but are not limited to, compounds known to treat taupathies, anti-angiogenesis agents, anti-tumor agents, other cancer treatments and autoimmune agents. Such compounds include, in general, but are not limited to, alkylating agents, toxins, antiproliferative agents and tubulin binding agents, Classes of cytotoxic agents for use herein include, for example, the anthracycline family of drugs, the vinca drugs, the mitomycins, the bleomycins, the cytotoxic nucleosides, the pteridine family of drugs, diynenes, the maytansinoids, the epothilones, and the podophyllotoxins.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof, U.S. patents and publications referenced herein are incorporated by reference.

EXAMPLES

Preparative RP-HPLC purification was conducted on YMC-Pack ODS-A columns (S-5 µM 300×20 mm ID) with gradient elution between 0% B to 50% B or 0% B to 100% B (A=–0.05% TFA in $H_2O$; B=0.05% TFA in $CH_3CN$) with gradient times of 10 min and a flow rate of 25 mL/min with UV 220 nm detection (Method 1). Analytical HPLC-MS was conducted on a YMC Combi-Screen 00DS-A column (S-5 µM, 50×4.6 mim ID) with gradient elution of % 0 B to 100% B (A=0.05% TFA in $H_2O$; B=0.05% TFA in $CH_3CN$) with gradient times of 10 min and a flow rate of 3,5 mL/min with UV 220 nm and Electrospray MS detection (Method 2).

Example 1

A. Synthesis of Paclitaxel C-10 Carbonylimidazole 2

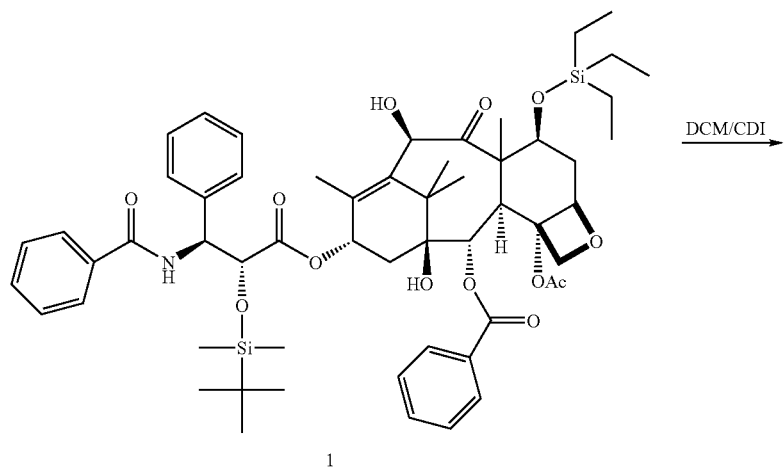

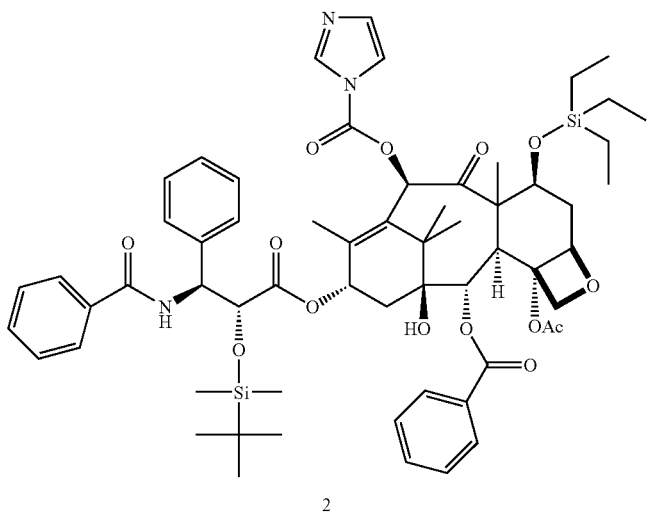

To 2'-O-TBS, 7-O-TES, 10-O-deacetyl-paclitaxel (845 mg, 0.81 mmol), in anhydrous DCM (6 ml.) was added carbonyl-diimidazole (530 mg, 400 mol %). The reaction mixture was allowed to stir for 16 hours at room temperature under nitrogen atmosphere, and then extracted with water (5 ml,). The organic layer was dried over sodium sulfate, filtered and concentrated to give 890 mg (96% yield) of 2, which was subsequently used without purification; $^1$H NMR (CDCl$_3$, 300 MHz) δ 8.26 (s, 1H), 8.18 (d, J=9 Hz, 2H), 7.77 (d, J=8 Hz, 2H), 7.53 (m, 1H), 7.14 (s, 1H), 7.09 (d, J=9 Hz, 1H), 6.59 (s, 1H), 6.32 (app t, J=9 Hz, 1H), 5.78 (m, 2H), 5.02 (d, J=8 Hz, 1H), 4.72 (d, J=2 Hz, 1H), 4.56 (m, 1H), 4.38 (d, J=8 Hz, 1H), 4.25 (d, J=8 Hz, 1H), 3.88 (d, J=7 Hz, 1H), 2.62 (s, 3H), 2.45 (m, 1H), 2.2 (In, 1H), 2.08 (s, 3H), 1.98 (m, 1H), 1.78 (s, 3H), 1.62 (s, 3H), 1.32 (m, 3H), 1.22 (s, 3H), 0.95 (m, 9H), 0.83 (s, 9H), 0.62 (m, 6H), 0.1 (s, 31H), −0.2 (s, 31H); Electrospray (LCMS) m/z 1134 (M+H$^+$, C$_{61}$H$_{80}$N$_3$O$_{14}$Si$_2$ requires 1134). retention time 9.92 min. (1% to 99% B. Method 2).

B. Synthesis of N1alkyl-N-3-acyl imidazolium 4
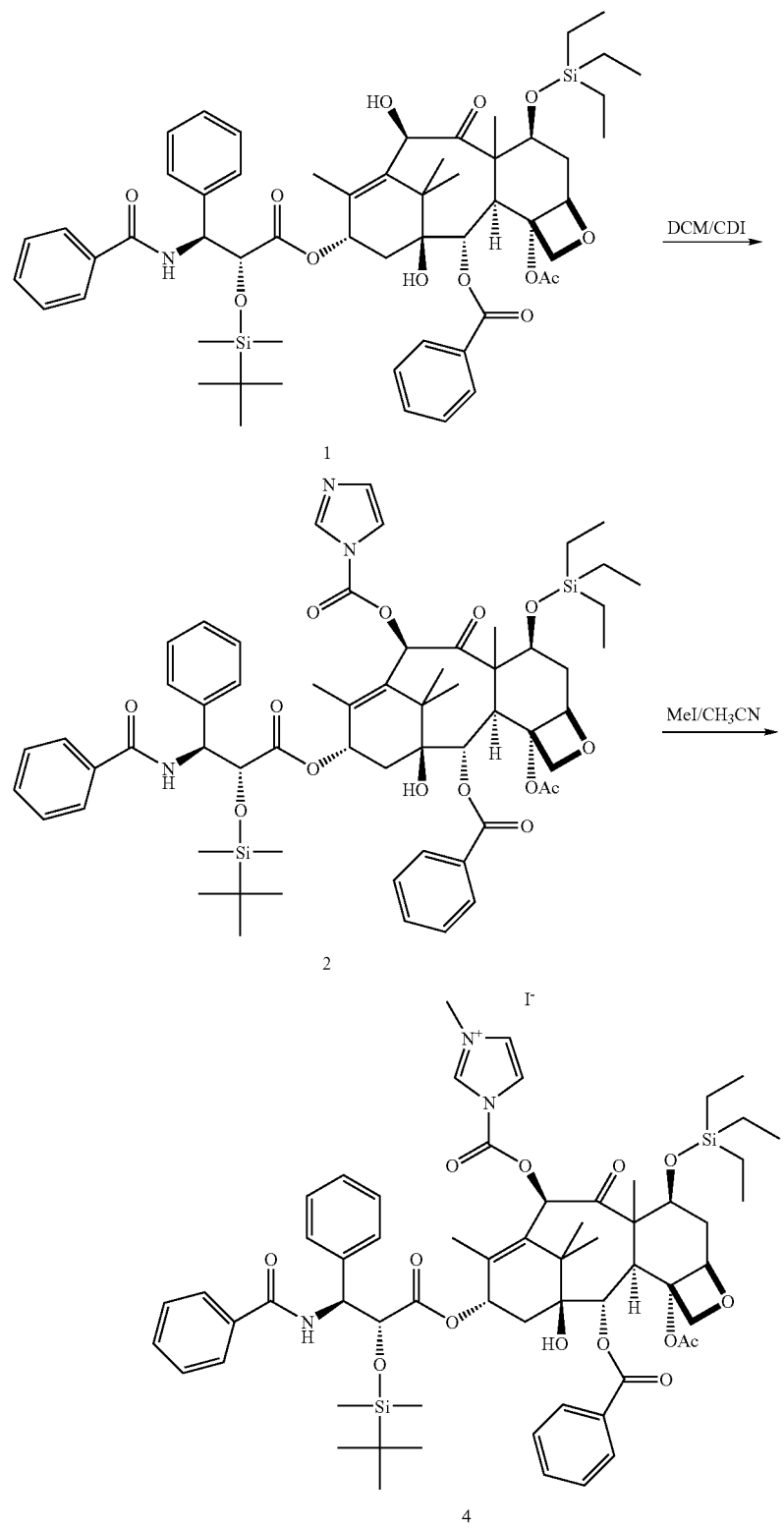

To a solution of 2'-O-TBS, 7-O-TES, 10-O-deacetyl-paclitaxel-10-O-carbonyl-imidazole (2, 200 mg, 0.176 mmol) in acetonitrile (2 mL) in a sealable tube was added methyl iodide (1 mL) and the resulting mixture was stirred for 3 h at 55° C. A stream of nitrogen was then used to remove the volatiles and the residue was held under high vacuum for 4 hours. The residue was then redissolved in anhydrous DMSO and used directly for carbamate formation.

C. Synthetic procedure for 10-O-deacetyl-paclitaxel-10-O-carbonyl-N-benzimidazole (Compound 8 in Table 1)

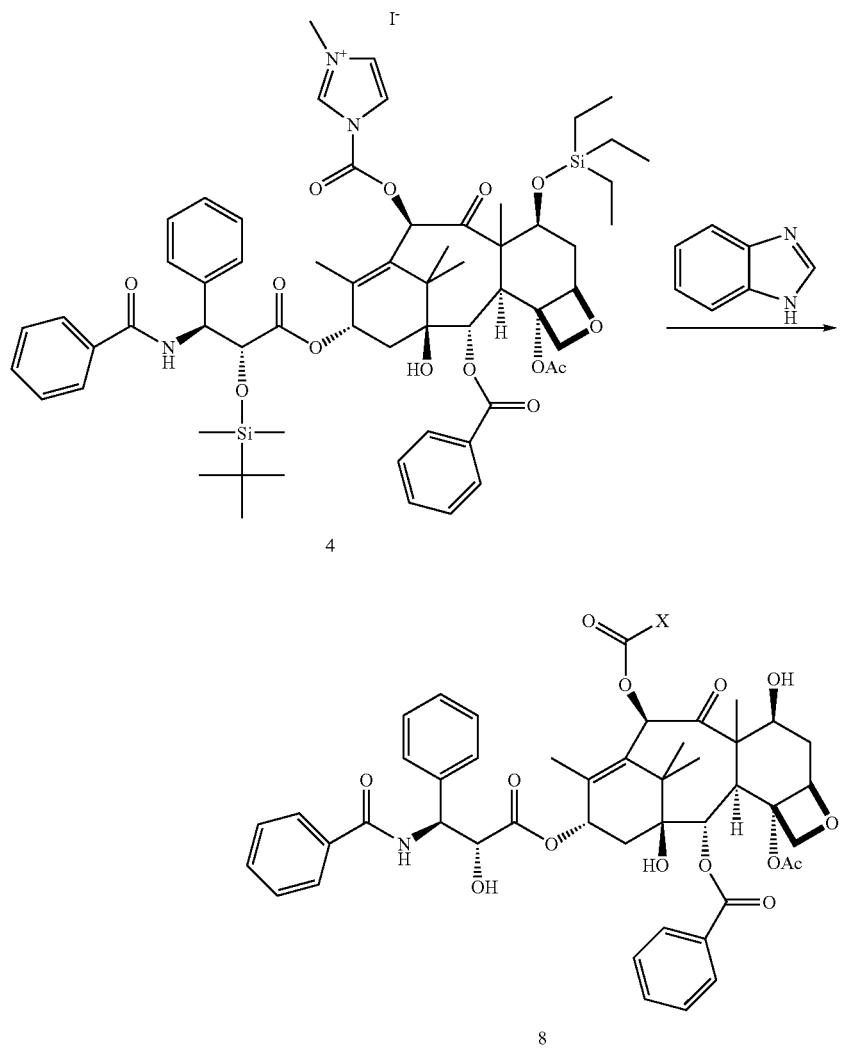

To a solution of 2'-O-TBS, 7-O-TES, 10-O-deacetyl-paclitaxel-10-O-carbonyl-methyl-imidazolinium iodide (4, 45 mg, 0.035 mmol), in anhydrous DMSO (0.4 mL) was added benzimidazole (13 mg, 300 mol %) followed by DIEA (6.1 μL, 300 mol %). The reaction mixture was stirred at room temperature for 30 min. until complete decoloration. The mixture was then diluted with pyridine (0.4 mL), cooled to 0° C. and treated with HF/pyridine (0.35 mL). The resulting solution was stirred for 3 h allowing the temperature to rise to room temperature. The mixture was then diluted with EtOAc (10 mL) and extracted with a saturated solution of $CuSO_4$ (3×2 ml.,) and water (3×2 mL). The organic solution was then dried over sodium sulfate, filtered and concentrated. The residue so obtained was purified by preparative RP-HPLC (Method 1).[17] Fractions containing the appropriate mass, as determined by analytical HPLC-MS (Method 2) were pooled and $CH_3CN$ removed under reduced pressure. The remaining aqueous mixture was then lyophilized obtaining 20 mg of the title compound (8) (59% overall yield). $^1$H NMR ($CDCl_3$, 300 MHz) δ 8.62 (s, 1H), 8.18 (d, 1=7 Hz, 2H), 8.06 (d, J=7 Hz, 1H), 7.82 (d, J=7 Hz, 1H), 7.77 (d, J=7 Hz, 21-F), 7.62 (m, 1H), 7.53 (m, 11H), 7.09 (d, J=9 Hz, 1H), 6.59 (s, 1H), 6.32 (app t, J=9 Hz, 1H), 5.78 (m, 2H), 5.02 (d, J=8 Hz, 1H), 4.82 (d, J=3 Hz, 1H), 4.56 (m, 1H), 4.38 (d, 1=8 Hz, 1H), 4.25 (d, J=8 Hz, 1H), 3.88 (d, J=7 Hz, 1H), 2.62 (m, 1H), 2.38 (m, 5H), 1.95 (m, 4H), 1.78 (s, 3H), 1.38 (s, 3H), 1.22 (s, 3H); Electrospray (LCMS) m/z 956 (M+H[30], $C_{53}H_{54}N_3O_{14}$ requires 956). retention time 6.55 min. (1% to 99% B, Method 2).

Several other C-10 carbamates of paclitaxel were prepared according to the procedure described herein. Table I below provides the structure of amine Xa used in the C-10 carbamate compounds provided herein. Also provided is HPLC and mass spectrometry data as well as ability of the compound to promote polymerization of tubulin, expressed as percentage of the activity of paclitaxel for exemplary compounds.

TABLE 1

| | Paclitaxel C-10 carbamates | | | | |
|---|---|---|---|---|---|
| Compound No. | Amine Xa | HPLC-RT[a] | Mass (expected) | Mass (observed) | MPA[b] |
| 1a | H₂N–(CH₂)₃–O–(CH₂CH₂O)₂–(CH₂)₃–NH–Cbz | 6.72 | 1192 (H⁺) | 1192 | a |
| 2a | H₂N–CH₂CH₂–O–CH₂CH₂–OH | 5.50 | 943 (H⁺) | 943 | b |
| 3a | alanine methyl ester | 5.97 | 941 (H⁺) | 941 | B |
| 4a | glutamic acid | 5.43 | 985 (H⁺) | 985 | a |
| 5 | 2-amino sugar (glucosamine) | 5.11 | 1017 (H⁺) | 1017 | a |
| 6 | piperidine | 6.54 | 923 (H⁺) | 923 | b |
| 7 | morpholine | 5.75 | 925 (H⁺) | 925 | a |
| 8 | benzimidazole | 6.55 | 956 (H⁺) | 956 | b |
| 9 | aniline | 6.48 | 931 (H⁺) | 931 | b |
| 10 | 4-aminophenylacetic acid | 6.08 | 989 (H⁺) | 989 | a |

TABLE 1-continued

Paclitaxel C-10 carbamates

| Compound No. | Amine Xa | HPLC-RT[a] | Mass (expected) | Mass (observed) | MPA[b] |
|---|---|---|---|---|---|
| 11 | (5-aminofluorescein structure) | 6.52 | 1207 (Na⁺) | 1207 (Na⁺) | c |
| 12 | H₂N-CH₂-C(O)-OH | 5.51 | 913 (H⁺) | 913 | N/A |
| 13 | CH₃-NH-CH₂-C(O)-OH | 5.57 | 927 (H⁺) | 927 | N/A |
| 14 | H₂N-CH₂-C(O)-O-tBu | 6.46 | 969 (H⁺) | 969 | b |
| 15 | H₂N-CH₂-C(O)-N(CH₃)₂ | 5.51 | 940 (H⁺) | 940 | N/A |
| 16 | H₂N(CH₂)₃NH(CH₂)₄NH(CH₂)₃NH₂ | 4.45 | 1040 (H⁺) | 1040 | a |
| 17 | (bis-Cbz spermine structure) | 6.14 | 1308 (H⁺) | 1308 | c |
| 18 | 4-nitroaniline | 6.54 | 976 (H⁺) | 976 | b |

TABLE 1-continued

Paclitaxel C-10 carbamates

| Compound No. | Amine Xa | HPLC-RT[a] | Mass (expected) | Mass (observed) | MPA[b] |
|---|---|---|---|---|---|
| 19 | (L-lysine with N-ε-Cbz protecting group) | 6.48 | 1118 (H⁺) | 1118 | a |
| 20 | (L-lysine) | 5.09 | 984 (H⁺) | 984 | a |
| 21 | (glucosamine with 6-aminohexanoyl group) | 5.18 | 1130 (H⁺) | 1130 | a |
| 22 | N-methylbutylamine | 6.77 | 926 (H⁺) | 926 | a |
| 23 | diethylamine | 6.42 | 911 (H⁺) | 911 | c |
| 24 | 1-amino-2-propanol | 5.48 | 913 (H⁺) | 913 | |
| 25 | (amino-PEG-carboxylic acid) | 5.69 | 1103.7 (H⁺) | 1103.4 | a |
| 26 | 6-aminohexanoic acid | 5.99 | 969 (H⁺) | 969 | a |
| 27 | ethylenediamine | 4.96 | 898 (H⁺) | 898 | N/A |

TABLE 1-continued

| | Paclitaxel C-10 carbamates | | | | |
|---|---|---|---|---|---|
| Compound No. | Amine Xa | HPLC-RT[a] | Mass (expected) | Mass (observed) | MPA[b] |
| 28 | *(structure shown)* | 5.49 | 1031 (H+) | 1031 | 40% |
| 29 | *(structure shown)* | 6.76 | 7680 (Average) | 7300 (Average) | a |
| 30 | *(structure shown)* | 5.52 | 939 (H+) | 939 | N/A |
| 31 | *(structure shown)* | 5.65 | 941 (H+) | 941 | N/A |

TABLE 1-continued

Paclitaxel C-10 carbamates

| Compound No. | Amine Xa | HPLC-RT[a] | Mass (expected) | Mass (observed) | MPA[b] |
|---|---|---|---|---|---|
| 32 | HO-C(=O)-C(CH$_3$)$_2$-NH- | 5.83 | 955 (H$^+$) | 955 | N/A |
| 33 | 3-aminopyridine | 5.08 | 932 (H$^+$) | 19.9 | N/A |

[a] Analylical HPLC-MS Method 2 (see Experimental)
[b] Ability of the compound to promote polymerization of tubulin, expressed as percentage of the activity of paclitaxel.
Average % is provided as follows:
a > 70%,
b = 30-70%,
c < 40% and
N/A = not available.

According to the procedure described herein, C-7 carbamates of paclitaxel were prepared for comparative purpose. Table 2 below provides HPLC and mass spectrometry data for exemplary C-7 carbamates.

TABLE 2

Paclitaxel C-7 carbamates

| Compound No. | Amine | HPLC-RT[a] | Mass (expected) | Mass (observed) |
|---|---|---|---|---|
| 1b | H$_2$N-CH$_2$-C(=O)-OH | 5.75 | 955 (H$^+$) | 955 |
| 2b | glutamic acid | 5.64 | 1027 (H$^+$) | 1027 |

A comparative compound TX-67 was prepared as described in Rice et al. *J. Med. Chem*, 2005, 48, 832-838 and has the following structure:

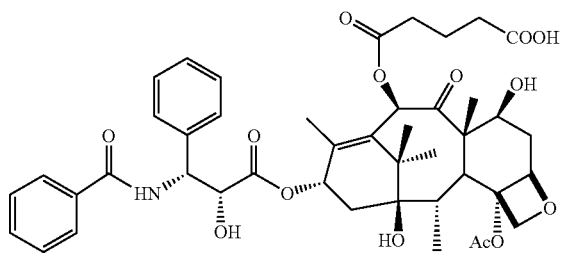

Example 2

Biological Assay

All compounds and controls were run in triplicates. The following controls have been used:

1) No drug and no rlhodamine; 2) rhodamine alone; 3) rhodamine and paclitaxel. Control #3 is a positive control (paclitaxel is a substrate for Pgp). The test compounds used were: compound 10, paclitaxel C-10 succinate monoester (TX-67, Rice et al. J. Med. Chem., 2005, 48, 832-838), compounds 1b, 13, 14, 15, 4a and 2b in Tables 1 and 2.

The experiment was run in two 24-wells plates. Test compounds were tested at 25 micromolar concentration. After addition of the test compounds, cells were incubated for 45 min. After this time the drug solutions were removed by aspiration. The monolayers were then rinsed three times with ice-cold PBSG and finally solubilized with 1 mL of lysing solution for 30 min. Cell lysates were assayed using Gemini EM platereader at excitation wavelength of 485 nm/520 nm. 50 uL of lysate was then assayed to calculate the amount of protein present and the Rhodamine 123 fluorescence was normalized to protein content. Table 4 provides data for exemplary compounds on their ability to affect the rhodamine 123 uptake in Bovine Brain Endothelial Cell (BBEC).

Cytotoxicity Assay (Monolayer)

Monolayer assays with tumor cell lines (MCF-7 breast carcinoma and HT-29 colorectal carcinoma from ATCC) were carried out in triplicate in 96-well plates with PMI1640 medium containing 5% fetal bovine serum, 100 U/ml penicillin and 100 µg/ml streptomycin. Normal human foreskin fibroblasts (HFF #CC-2509) were from Cambrex and were cultured in FGM-2 medium. Exponentially growing cells (5,000 MCF-7 or HT-29; 1,500 HFF) were plated in 100 µl medium and incubated overnight (5% CO$_2$, 37° C.). Compounds (20 pM to 20 µM final concentration, 6-8 doses) and vehicle (DMSO) controls were added and the incubation was continued for an additional 72 hours. Final cell density was determined by incubating cultures with 25 µl AlamarBlue reagent (BioSource, Camarillo, Calif.) for 4 hours, followed by determination of fluorescence at excitation of 544 nm and emission of 590 nm with a SpectroMax Gemini EM fluorescence plate reader (Molecular Devices, Sunnyvale, Calif.). $EC_{50}$ values were generated from dose-response curves by a 4-parameter method using Softmax PRO software, Mean FC50s (±SD) represent the average of all tests carried out for all lots of a given compound. Outlier $EC_{50}$ values (<7%) were identified and removed prior to analysis using the method of Hoaglin et al., *J. Amer. Statistical Assoc.*, 81, 991-999 (1986).

Cytotoxicity Assay Protocols

1. Cells:
  a. Breast tumor cell lines, MCF-7 and NCI/ADR-RES
  b. Colon tumor cell lines: HCT-15 and HT-29
  c. Leukemia cell line K562 and K562/R
  d. Non-small cell lung cancer cell line A549
  e. Human foreskin fibroblast cells (HFF)
  f. Human umbilical vein endothelial cells (HUVEC)
2. Cell Culture:
  a. All tumor cells were grown in RPMI1640 medium supplemented with 5% (v/v) fetal bovine serum and the antibiotics in a final concentration of 100 U/ml of penicillin and 100 µg/ml of streptomycin in an atmosphere of 5% $CO_2$.
  b. HFF and HUVEC were grown in the medium of FGM-2 and EGM-2 from Cambrex,
3. Cytotoxicity Assay:
  a. Day 1: Cells growing exponentially were transferred to 96-well tissue culture plates. All cell types were plated at a density of 1,500-5,000 cells per well in 100 µl complete medium.
  b. Day 2: 100 µl of experimental compounds in complete medium was added in triplicate wells,
  c. Day 5: Cell growth inhibition was assayed using the AlamarBlue (BioSource, Camarillo, Calif.) signal reduction assay. Correlation between AlamarBlue and cell proliferation has been established in the literature. Compound concentration versus relative fluorescence units was plotted. The EC50, indicated by the inflection point of the curve, is the concentration alt which growth is inhibited by 50%.

Table 3 provides results for cytotoxicity assay for exemplary compounds and paclitaxel. Detailed procedures for conducting the assays are provided herein and are known in the art.

TABLE 3

Results of cytotoxicity assay

| Compound No. | COMPOUND NAME | EC50+ (µM) |
|---|---|---|
|  | PXL (20 mM stock) | a |
| 5 | PXL-10Ca-Glucosamine | c |
| 23 | PXL-10Ca-di-Et-amine | b |
| 18 | PXL-10Ca-p-NO2-aniline | b |
| 9 | PXL-10Ca-aniline | b |
| 39 | PXL-10Ca-alanine-Me-ester | a |
| 6 | PXL-10Ca-piperidine | a |
| 22 | PXL-10Ca-N-methyl-N-butylamine | a |
| 29 | PXL-10Ca-PEG(5)-OH | b |
| 7 | PXL-10Ca-Morpholine | b |
| 28 | PXL-10Ca-PEG(29)-VBL | b |
| 21 | PXL-10Ca-Alk(6)Am(2)-glucosamine | c |
| 10 | PXL-10Ca-Ph-acetic acid | c |
| 19 | PXL-10Ca-Z-Lys-OH | c |
| 20 | PXL-10Ca-H-Lys-OH | c |
| 29 | PXL-10Ca-PEG6000-10Ca-PXL | c |
| 16 | PXL-10CaSpermine | c |
| 25 | PXL-10Ca-PEG(14)-COOH | c |
| 14 | PXL-10Ca-Gly(tBu) | b |
| 13 | PXL-10Ca-Sar-OH | c |

TABLE 3-continued

Results of cytotoxicity assay

| Compound No. | COMPOUND NAME | EC50+ (µM) |
|---|---|---|
| 15 | PXL-10Ca-Gly-N(Me)2 | b |
| 12 | PXL-10Ca-Gly-OH | c |
|  | PXL-10Ca-Glu | b |

+Average EC50 is provided as follows: a < 0.01 µM, b = 0.01-0.5 µM and c > 0.5 µM

TABLE 4

Results of rhodamine 123 uptake assay

| Compound No. | Rhodamine 123 uptake++ |
|---|---|
| R123* | b |
| PXL** | b |
| paclitaxel C-10 succinate monoester*** | a |
| 12 | a |
| 1b | b |
| 13 | b |
| 14 | b |
| 15 | a |
| 4a | b |
| 2b | a |

++Average rhodamine 123 uptake is provided as follows: a < 0.25 and b = >0.25
*Rhodamine 123;
**paclitaxel
***The compound is a comparative example designated as TX-67 in Rice et al. J. Med. chem, 2005, 48, 832-838, structure provided elsewhere herein.

The positive control (PXL) worked as expected showing higher rhodamine uptake. Compound TX-67, a10-O-deacetylpaclitaxel 10-monosuccinyl ester did not show any effect on rhodamine uptake. In certain embodiments, the exemplary compounds increased rhodamine 123 uptake similarly to the positive control indicating that these compounds are able to cross the cell membrane and therefore it is likely that they would be able enter the cells. It indicates that C-10 modification is required to impair the Pgp interaction.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound of formula 1:

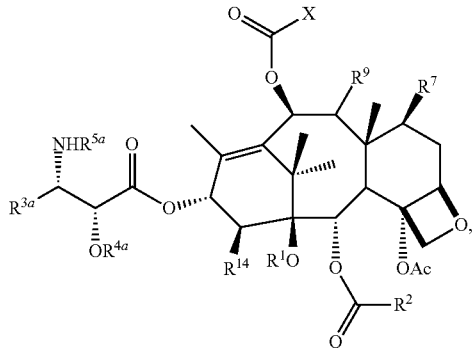

or pharmaceutically acceptable compound, wherein $R^1$ is hydrogen, alkyl, alkenyl, alkynyl, cycloalkyl, heterocyclyl, aryl, heteroaryl or acyl;

$R^2$ is alkyl or aryl, wherein the aryl group is optionally substituted with one to three electron withdrawing or electron donating groups;

$R^7$ is H or $OR^{7a}$ where $R^{7a}$ is hydrogen, alkyl, alkenyl, alkynyl, cycloalkyl, heterocyclyl, aryl, heteroaryl, —$COR^{7b}$, —$CONR^{7c}R^{7d}$ or is hydroxyl protecting group, wherein $R^{7b}$ is alkyl, alkenyl, alkynyl, cycloalkyl, heterocyclyl, aryl or heteroaryl, and $R^{7c}$ and $R^{7b}$ are each independently selected as follows:

a) $R^{7c}$ and $R^{7d}$ are each independently hydrogen, alkyl, alkenyl, alkynyl, cycloalkyl, heterocyclyl, aryl or heteroaryl, or b) $R^{7c}$ and $R^{7d}$ together with the nitrogen atom form an optionally substituted 5-7 membered heterocyclic or heteroaryl ring;

$R^9$ is =O, or —$OR^{7a}$;

X is $NR^xR^y$, where $R^x$ is hydrogen or alkyl and $R^y$ is carboxyalkyl, carboxyheteroalkyl, carboxyalkenyl, carboxyalkynyl, carboxycycloalkyl, carboxyheterocyclyl, carboxyaryl, carboxyheteroaryl or aminoheteroalkyl, wherein the amino group is optionally protected with a protecting group;

$R^{14}$ is hydrogen, hydroxyl or alkoxy;

$R^{3a}$ is alkyl, alkenyl, alkynyl, cycloalkyl, heterocyclyl, aryl or heteroaryl;

$R^{4a}$ is hydrogen, alkyl, alkenyl, alkynyl, cycloalkyl, heterocyclyl, aryl, heteroaryl or is hydroxyl protecting group;

$R^{5a}$ is —$COR^{7b}$, —$COOR^{7b}$, or $CONR^{7c}R^{7d}$; and $R^1$, $R^2$, $R^{3a}$, $R^{4a}$, $R^{5a}$, $R^{7a}$, $R^{7b}$, $R^{7c}$, $R^{7d}$, $R^y$, and $R^{14}$ are unsubstituted or substituted with 1-4 substituents $Q^1$, wherein each $Q^1$ is independently halo, pseudohalo, hydroxy, oxo, thia, nitrile, amino, nitro, formyl, mercapto, hydroxycarbonyl, hydroxycarbonylalkyl, alkyl, haloalkyl, aminoalkyl, diaminoalkyl, cycloalkyl, cycloalkylalkyl, heterocyclyl, heterocycclylalkyl, aryl, heteroaryl, aralkyl, heteroarylalkyl, alkylcarbonyl, arylcarbonyl, heteroarylcarbonyl, alkoxycarbonyl, aralkyloxycarbonyl, aralkoxycarbonylamino, aminocarbonyl, alkoxy, aryloxy, heteroaryloxy, heteroaralkoxy, heterocyclyloxy, cycloalkoxy, aralkoxy, alkylamino, dialkylamino, haloalkylamino, arylamino, diarylamino or alkylarylamino with the proviso that when $R^1$ is hydrogen, $R^2$ is aryl, $R^{3a}$ is aryl, $R^{4a}$ is hydrogen, $R^{5a}$ is —$COR^{7b}$, $R^{7b}$ is aryl, $R^7$ is —OH, and $R^9$ is =O, X is $NR^xR^y$, and Rx is hydrogen, then $R^y$ is not aminoheteroalkyl.

2. The compound of claim 1, wherein $R^1$ is hydrogen or alkyl;

$R^2$ is alkyl or aryl group;

$R^7$ is H, OH or alkoxy;

$R^9$ is =O, OH or alkoxy;

$R^{14}$ is hydrogen;

$R^{3a}$ is alkyl, alkenyl or aryl;

$R^{4a}$ is hydrogen; and $R^{5a}$ is alkoxycarbonyl or arylcarbonyl.

3. The compound of claim 1, wherein $R^1$ is hydrogen.

4. The compound of claim 1, wherein $R^2$ is lower alkyl or aryl.

5. The compound of claim 1, wherein $R^2$ is phenyl.

6. The compound of claim 1, wherein $R^7$ is hydroxyl.

7. The compound of claim 1, wherein $R^9$ is =O.

8. The compound of claim 1, wherein $R^{14}$ is hydrogen.

9. The compound of claim 1, wherein $R^{3a}$ is aryl, alkyl, haloalkyl, alkenyl or haloalkenyl.

10. The compound of claim 1, wherein $R^{3a}$ is phenyl.

11. The compound of claim 1, wherein $R^{5a}$ is alkoxycarbonyl or arylcarbonyl.

12. The compound of claim 1, wherein $R^{5a}$ is tert-butyloxycarbonyl or phenylcarbonyl.

13. The compound of claim 1, wherein $R^x$ hydrogen and $R^y$ is carboxyalkyl or dicarboxyalkyl, optionally substituted with one to three groups selected from amino, araloxycarbonylaminoalkyl, aminoalkyl and cycloalkyl.

14. The compound of claim 1, wherein X is:

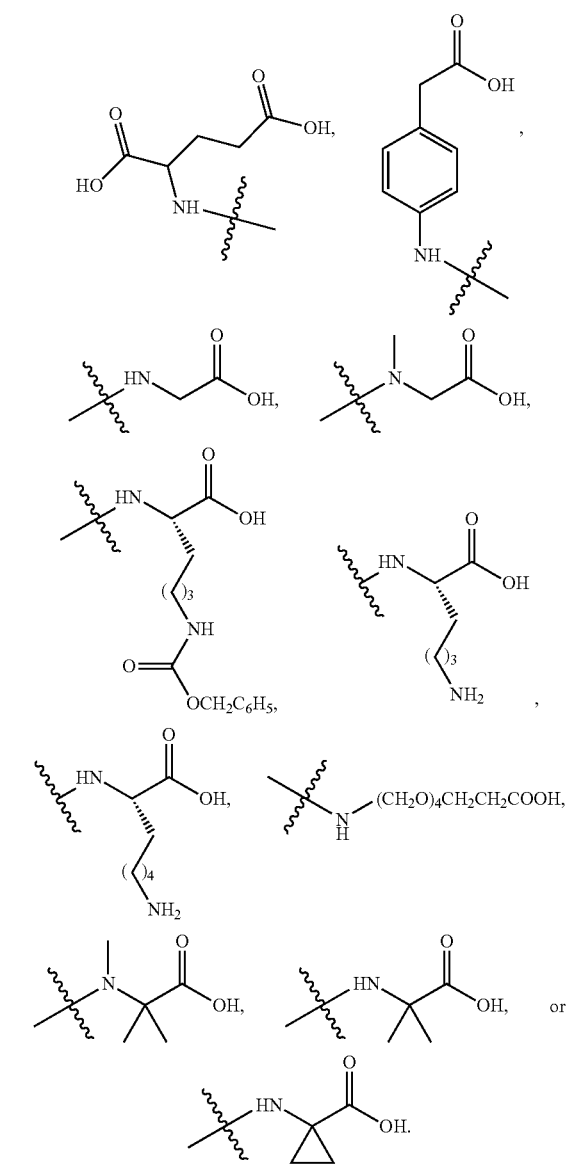

15. The compound of claim 1, wherein the compound has the formula
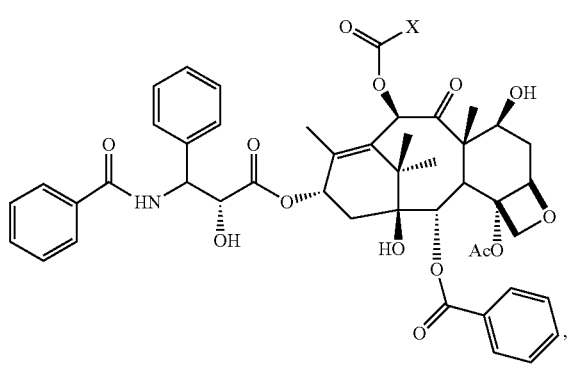
wherein X is
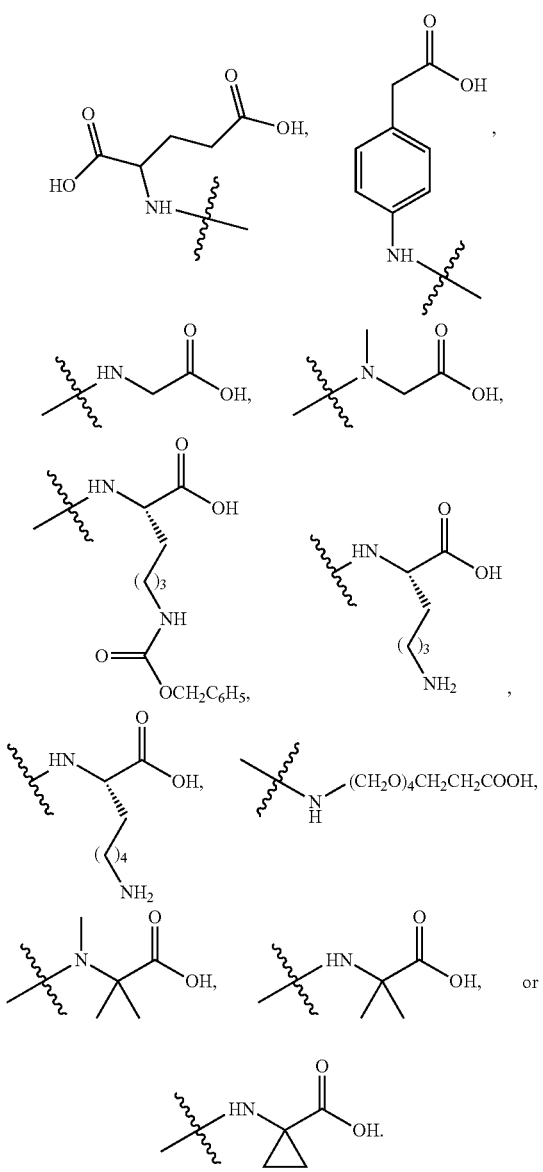
16. The compound of claim 1, wherein X is:
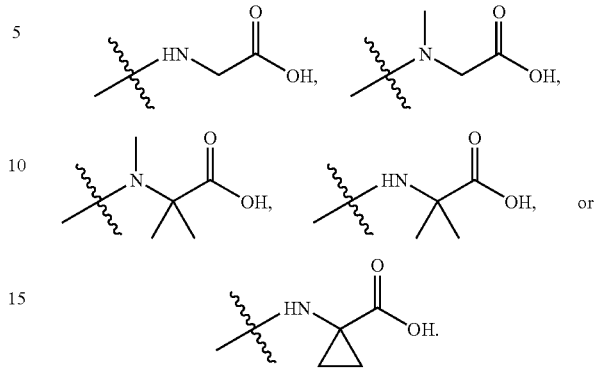
17. The compound of claim 1, wherein X is:
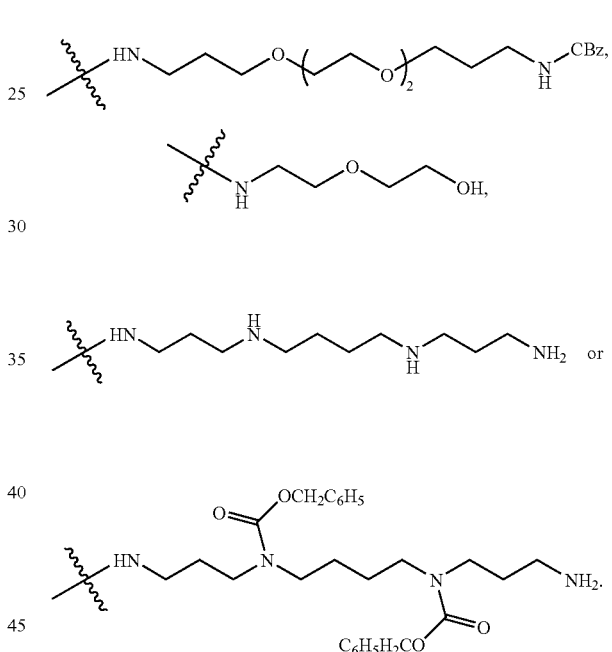
18. A compound of formula 1a:
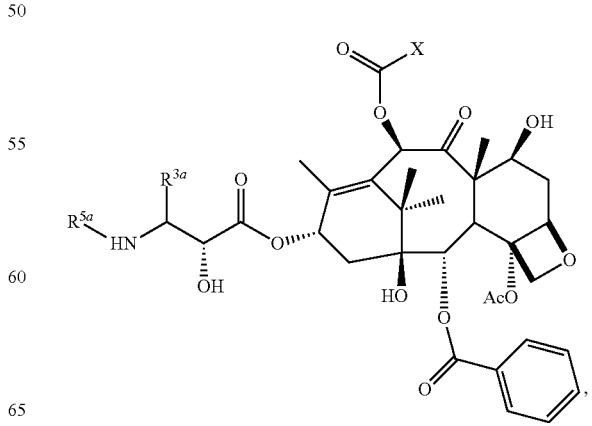

or pharmaceutically acceptable compound thereof, wherein X is glucosamine, or is $NR^xR^y$, where $R^x$ is hydrogen or lower alkyl and $R^y$ is alkyl substituted with one to three substitutents selected from hydroxy, amino, alkylaminocarbonyl, dialkylaminocarbonyl, aralkoxycarbonyl, alkoxycarbonyl, aralkoxycarbonylamino, and heterocyclylaminocarbonyl, wherein the heterocyclyl group contains a 5 to 7 membered ring containing one or two heteroatoms selected from N and O and is optionally substituted with 1 to 4 hydroxy or hydroxyalkyl groups, $R^{3a}$ is alkyl, alkenyl, alkynyl, cycloalkyl, heterocyclyl or phenyl;

$R^{5a}$ is —$COR^{7b}$, —$COOR^{7b}$ or —$CONHR^{7b}$;

$R^{7b}$ is alkyl, alkenyl, alkynyl, cycloalkyl, heterocyclyl or aryl;

and $R^{3a}$, $R^{5a}$ and $R^{7b}$ are unsubstituted or substituted with 1-4 substituents $Q^1$, wherein each $Q^1$ is independently is halo, pseudohalo, hydroxy, amino, nitro, alkyl, haloalkyl, aminoalkyl, diaminoalkyl, cycloalkyl, heterocycly, stryl, heteroaryl, aralkyl, alkylcarbonyl, arylcarbonyl, heteroarylcarbonyl, alkoxycarbonyl, aralkyloxycarbonyl or aralkoxycarbonylamino with the proviso that when $R^{3a}$ is aryl, $R^{5a}$ is —$COR^{7b}$, $R^{7b}$ is aryl, X is $NR^xR^y$, and $R^x$ is hydrogen, then Ry is not aminoheteroalkyl and when $R^{3a}$ is aryl, $R^{5a}$ is —$COR^{7b}$, and $R^{7b}$ is aryl, X is not gluxosamine.

19. The compound of claim 18 wherein $R^{3a}$ is alkyl, alkenyl or aryl; and $R^{5a}$ is alkoxycarbonyl or arylcarbonyl.

20. The compound of claim 18, wherein $R^{3a}$ is aryl or alkyl.

21. The compound of claim 18, wherein $R^{3a}$ is phenyl.

22. The compound of claim 18, wherein $R^{5a}$ is alkoxycarbonyl or arylcarbonyl.

23. The compound of claim 18, wherein $R^{5a}$ is tert-butyloxycarbonyl or phenylcarbonyl.

24. The compound of claim 18, wherein $R^x$ is hydrogen and $R^y$ is hydroxyalkyl, aminoalkyl, dialkylaminocarbonylalkyl, alkyloxycarbonylalkyl, or heterocyclylaminocarbonylalkyl, wherein the heterocyclyl group contains a 5 to 7 membered ring containing one or two heteroatoms that is N or O and is optionally substituted with 1 to 4 hydroxy or hydroxyalkyl groups.

25. The compound of claim 18, wherein X is:

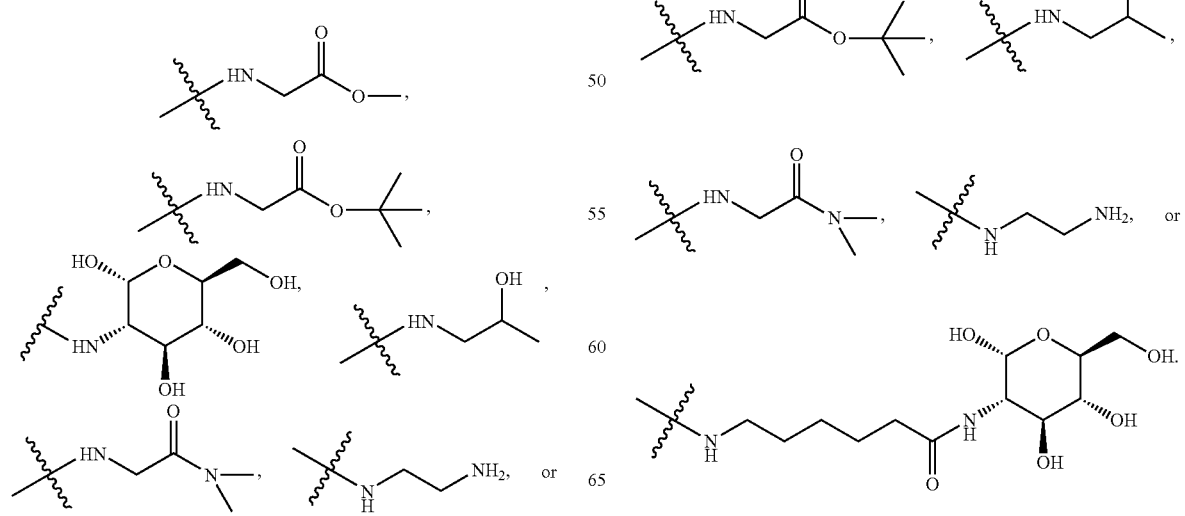

26. The compound of claim 18, wherein the compound has the formula:

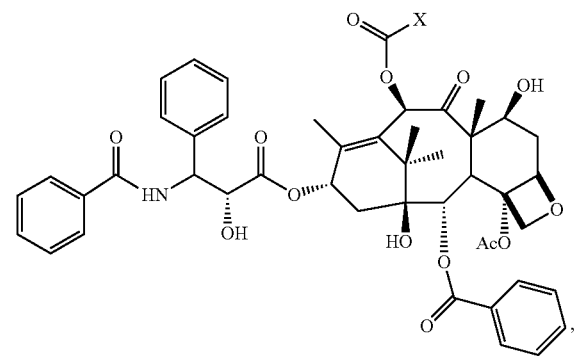

wherein X is:

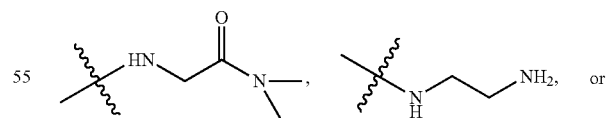

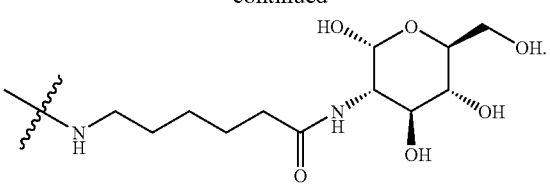

27. The compound of claim 1, wherein the compound has formula 1b:

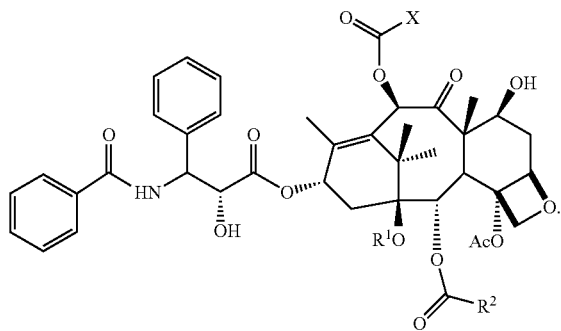

28. The compound of claim 1, wherein the compound has formula 1c:

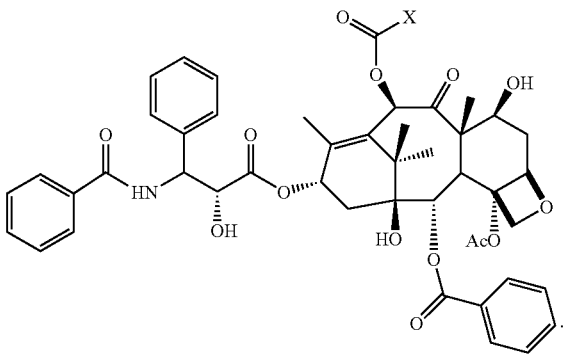

29. The compound of claim 1, wherein the compound has formula 1d:

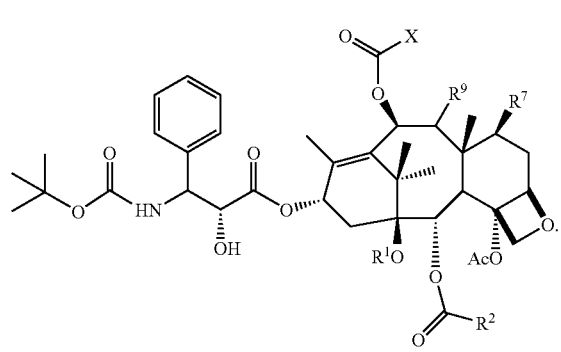

30. The compound of claim 1, wherein the compound has formula 1f:

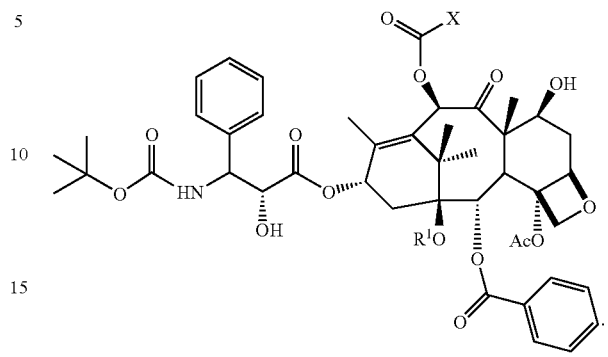

31. A pharmaceutical composition comprising a compound of claim 1 or 18 in a pharmaceutically acceptable carrier.

32. A method for inhibiting P-glyocoprotein comprising administering a compound of claim 1 or 18 or a pharmaceutically acceptable compound thereof.

33. A method for treatment of taupathy, comprising administering a compound of claim 1 or 18 or a pharmaceutically acceptable compound thereof.

34. The method of claim 33, wherein the taupathy is associated with Alzheimer disease, Pick's disease, corticobasal degeneration, progressive supranuclear palsy or frontotemporoparietal dementia.

35. A method for treatment of cancer comprising administering a compound of claim 1 or 18 or a pharmaceutically acceptable compound thereof.

36. The method of claim 35, wherein the cancer is non-small cell lung cancer, small cell lung cancer, head and neck squamous cancer, colorectal cancer, prostate cancer, breast cancer, acute lymphocytic leukemia, adult acute myeloid leukemia, adult non-Hodgkin's lymphoma, brain tumor, cervical cancer, childhood cancer, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, cancer or small-cell lung cancer.

37. An article of manufacture, comprising packaging material, the compound of claim 1 or 18, or a pharmaceutically acceptable compound thereof; contained within packaging material.

\* \* \* \* \*